(12) United States Patent
Zhu et al.

(10) Patent No.: US 11,570,987 B2
(45) Date of Patent: Feb. 7, 2023

(54) PESTICIDAL COMPOUNDS AND METHODS OF USE

(71) Applicant: New York University, New York, NY (US)

(72) Inventors: Xiaolong Zhu, New York, NY (US); Jingxiang Yang, New York, NY (US); Michael D. Ward, New York, NY (US); Bart Kahr, Brooklyn, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 17/033,317

(22) Filed: Sep. 25, 2020

(65) Prior Publication Data

US 2021/0092950 A1  Apr. 1, 2021

Related U.S. Application Data

(60) Provisional application No. 62/907,185, filed on Sep. 27, 2019.

(51) Int. Cl.
*A01N 31/04* (2006.01)
*C07C 33/46* (2006.01)

(52) U.S. Cl.
CPC .............. *A01N 31/04* (2013.01); *C07C 33/46* (2013.01)

(58) Field of Classification Search
CPC ................................ A01N 31/04; C07C 33/46
See application file for complete search history.

(56) References Cited

FOREIGN PATENT DOCUMENTS

GB           685133      * 12/1952  ............. C07C 33/46

OTHER PUBLICATIONS

Casida, J. E. Michael Elliott's billion dollar crystals and other discoveries in insecticide chemistry. Pest. Manag. Sci. 2010, 66, 1163-1170.
Gravitz, L. Vector control: the last bite. Nature, 2012, 484, S26-S27.
Heckel, D. G. Insecticide resistance after Silent Spring. Science 2012; 337: 1612-1614.
Lopez-Mejías, V.; Kampf, J. W.; Matzger, A. J. Polymer-induced nucleation of tolfenamic acid: structural investigation of a pentamorph. J. Am. Chem. Soc. 2009, 131, 4554-4555.
Sparks, T. C; Insecticide discovery: An evaluation and analysis. Pestic. Biochem. Physiol. 2013, 107, 8-17.
Zhu X, et al., "Manipulating Solid Forms of Contact Insecticides for Infectious Disease Prevention," J. Am. Chem. Soc. 2019, 141, 16858-16864.

* cited by examiner

*Primary Examiner* — Yong L Chu
(74) *Attorney, Agent, or Firm* — Troutman Pepper Hamilton Sanders LLP

(57) ABSTRACT

Described herein are compounds, pesticidally acceptable salts thereof, and compositions thereof that are useful, for example, for pest management and for controlling pests. In certain embodiments provided are enantioenriched and/or enantiopure compounds and pesticidally acceptable salts thereof, and methods of making same. Methods of controlling pests with the compounds of the disclosure are also provided.

18 Claims, 12 Drawing Sheets
(11 of 12 Drawing Sheet(s) Filed in Color)

a. Flow chart for the sighting study.

b. Flow chart for the main study.

PESTICIDAL COMPOUNDS AND METHODS OF USE

CROSS-REFERENCE TO RELATED APPLICATIONS

The present application claims priority to U.S. Provisional Application No. 62/907,185, filed Sep. 27, 2019, which is hereby incorporated by reference in its entirety.

STATEMENT AS TO FEDERALLY FUNDED RESEARCH

This invention was made with government support under grant number DMR-1470035 awarded by National Science Foundation's Materials Research Science and Engineering. The government has certain rights in the invention.

FIELD

Embodiments disclosed herein are directed to compounds, pesticidally acceptable salts thereof, and compositions comprising same, as well as their use for pest management and pest control.

BACKGROUND

DDT (1,1,1-trichloro-2,2-bis(4-chlorophenyl)ethane) is a well-known inexpensive pesticide. DDT was marshalled for the eradication of malaria by the World Health Organization (WHO) in 1955 (see WHO, Global Malaria Control and Elimination—Report of a Technical Review. Geneva: World Health Organization, 2008). DDT nevertheless faltered in the face of insect resistance, and experienced a backlash in the wake of serious environmental concerns, foretold by Rachel Carson in *Silent Spring* (see Heckel, D. G. Insecticide resistance after Silent Spring. *Science* 2012; 337: 1612-1614).

Gravitz and Sparks have emphasized the continuing need for new, inexpensive and long-lasting insecticides for indoor residual spraying and for insecticide-treated bed nets (see Gravitz, L. Vector control: the last bite. Nature, 2012, 484, S26-S27; see also Sparks, T. C; Insecticide discovery: An evaluation and analysis. Pestic. Biochem. Physiol. 2013, 107, 8-17).

There is a great need for the development of safe and more selective insecticides. The present embodiments described herein fulfill these needs and others.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application

SUMMARY OF THE DISCLOSURE

Various non-limiting aspects and embodiments of the disclosure are described below.

In one aspect, the present disclosure provides a compound according to Formula (I):

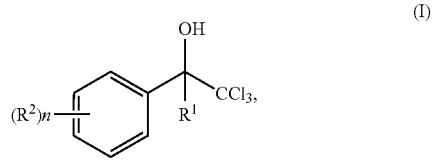

or a pesticidally acceptable salt thereof, wherein:

$R^1$ is selected from —H and —$CH_3$;

$R^2$ is independently at each occurrence selected from —F, —$OCF_3$, and —$CF_3$;

n is an integer from 1 to 5, with the proviso that the compound according to Formula (I) is not:

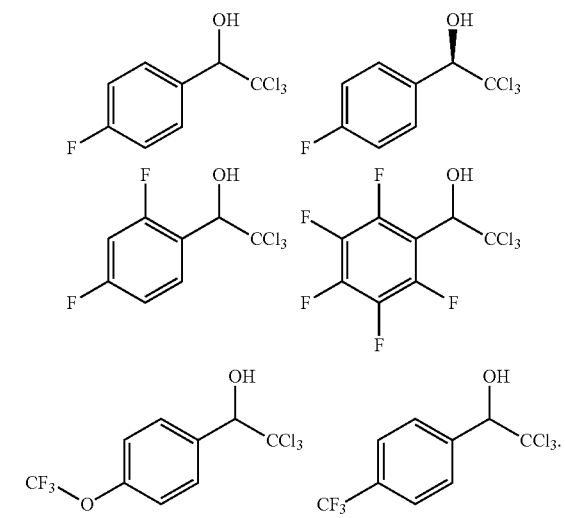

In one embodiment, $R^1$ is H. In one embodiment, $R^1$ is —$CH_3$. In one embodiment, $R^2$ is —F. In one embodiment, $R^2$ is —$OCF_3$. In one embodiment, $R^2$ is —$CF_3$.

In one embodiment, the compound is selected from the group consisting of:

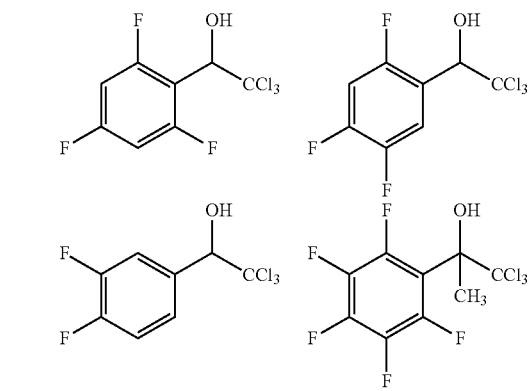

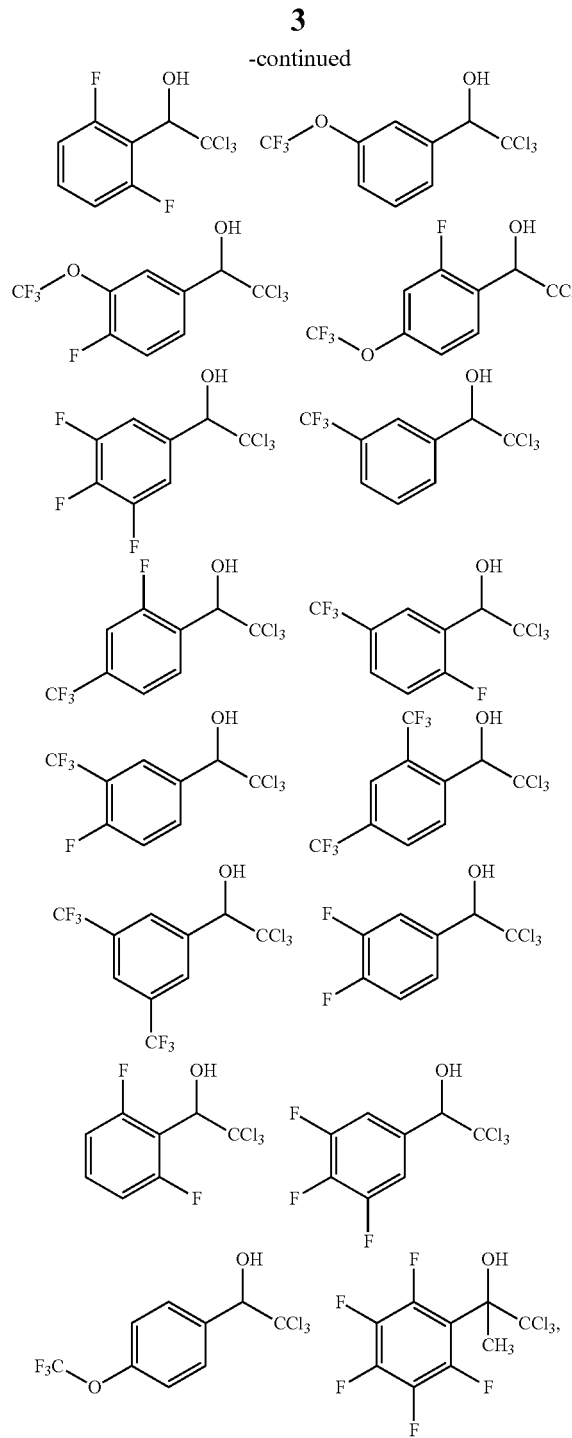

or a pesticidally acceptable salt thereof.

In another aspect, the present disclosure provides a pesticidal composition comprising the compound as described above, wherein the composition comprises a racemic mixture of the compound.

In one embodiment, the composition comprises an enantioenriched mixture of the compound. In one embodiment, the compound is present in an enantiomeric excess of about 90% or more.

In yet another aspect, the present disclosure provides a method of preparing an enantiomer of a compound according to Formula (II):

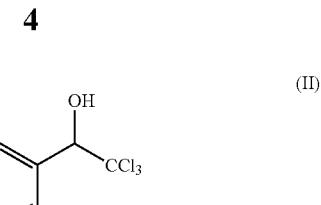

comprising the steps of:
a) reacting a compound of Formula (IIa):

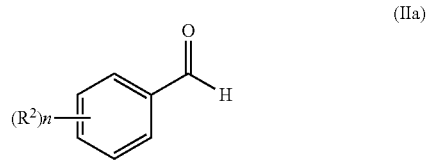

with trichloroacetic acid and sodium trichloroacetate to give a racemic mixture of the compound of Formula (II);
b) reacting the racemic mixture of the compound of Formula (II) with Dess-Martin reagent, thereby affording a compound of Formula (IIb):

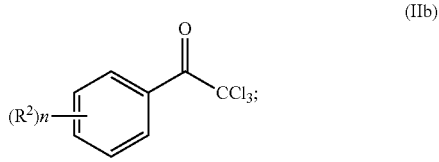

c) reacting the compound of Formula (IIb) with (R) oxazaborolidine or (S) oxazaborolidine;
d) reacting the mixture of step c) with catecholborane, and
e) isolating the enantiomer of the compound according to Formula (II).

In yet another embodiment, the present disclosure provides a method of controlling a pest comprising applying to the pest or its locus a compound according to formula (I):

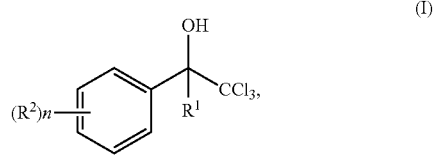

or a pesticidally acceptable salt thereof, wherein:
$R^1$ is selected from —H and —CH$_3$;
$R^2$ is independently at each occurrence selected from —F, —OCF$_3$, and —CF$_3$;
n is an integer from 1 to 5;
wherein the compound has an insecticidal knock down speed of at least twice as active, at least 3 times as active, at least 4 times as active, at least 5 times as active, at least 6 times as active, at least 7 times as active, at least 8 times as active, or at least 9 times as active as DDT.

In one embodiment, $R^1$ is —H. In one embodiment, $R^1$ is —CH$_3$. In one embodiment, $R^2$ is —F. In one embodiment, $R^2$ is —OCF$_3$. In one embodiment, $R^2$ is —CF$_3$.

In one aspect, the present disclosure provides a method of controlling a pest comprising applying to the pest or its locus the compound as described above.

In one embodiment, the pest is an insect.

In one embodiment, the insect is selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas (indoors & outdoors), flea beetles, flies, flesh flies, fruit flies, fungus gnats (sciarid flies), gnats, grasshoppers, green bottle flies, greenstriped mapleworms, ground beetles, gypsy moths (larvae), hide beetles, house flies, hornets, horseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, redhumped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellownecked caterpillar, wasps, and webworms.

These and other aspects of the present disclosure will become apparent to those skilled in the art after a reading of the following detailed description of the disclosure, including the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
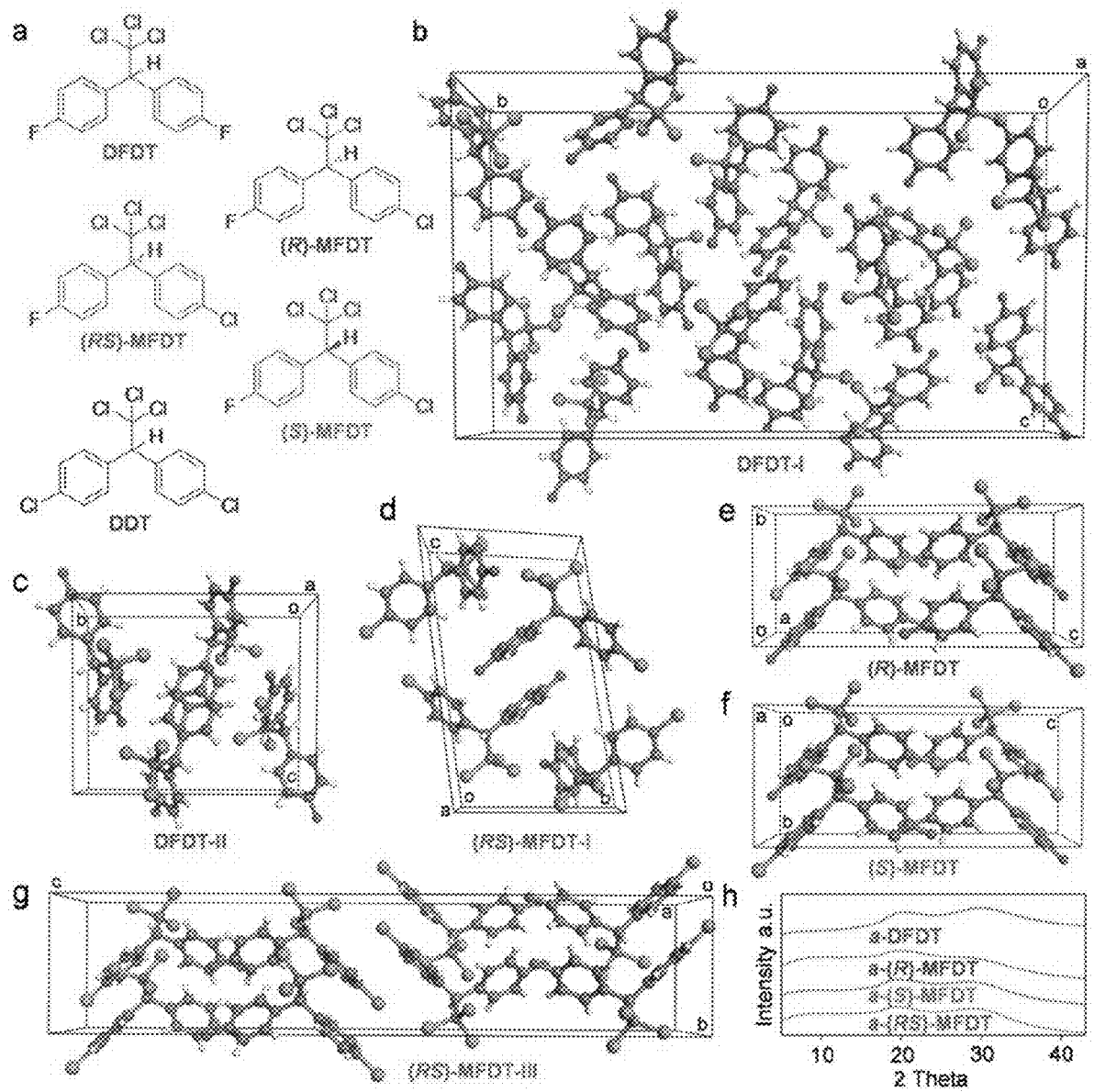
FIG. 1 illustrates solid-state forms of DFDT and MFDT.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "carrier" means a diluent, adjuvant, or excipient with which a compound is administered. The term "pesticidal carrier" means a carrier that facilitates, for example, the delivery and/or release of a pesticidal substance in the field of use. Examples of suitable carriers are but not limited to phytogel, hydrogel, mineral earths (e.g. silicate, silica gel, talc, kaolin, limestone, lime, chalk, red clay, loess, clay, dolomite, diatomaceous earth, Calcium sulfate, magnesium sulfate, magnesium oxide), ground synthetic materials, fertilizers (eg, NPK fertilizer, ammonium nitrate, calcium ammonium nitrate, ammonium nitrate, ammonium sulfate, ammonium sulfate or ammonium phosphate-containing inorganic fertilizers; liquid fertilizers, semi-liquid fertilizers, solid or liquid organic fertilizers such as manure, biogas and straw compost, earthworm dung, compost, seaweed or guano, or urea, formaldehyde urea, urea ammonium nitrate (UAN) solution, urea sulfur, stabilized urea, urea-based NPK fertilizer, or Urea-containing fertilizers such as ammonium urea sulphate), and products of botanical origin (eg cereal flour, bark flour, wood flour and nutshell flour, cellulose powder) and other solid carriers. Further suitable examples of carriers include, for example, fumed silica or precipitated silica which can be used in solid formulations as flow aids, anti-caking aids, grinding aids and as carriers for liquid active ingredients.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the phrase "integer from X to Y" means any integer that includes the endpoints. For example, the phrase "integer from X to Y" means 1, 2, 3, 4, or 5.

As used herein, the term "isolated" means that the compounds described herein are separated from other components of either (a) a natural source, such as a plant or cell, or (b) a synthetic organic chemical reaction mixture, such as by conventional techniques.

As used herein, the term "mammal" means a warm-blooded vertebrate animal including, but not limited to, a rodent (i.e., a mouse, a rat, or a guinea pig), a monkey, a cat, a dog, a cow, a horse, a pig, and a human.

As used herein the phrase "pesticidal or pesticidally acceptable" salt refers to any salt of a compound disclosed herein which retains its biological properties and which is not toxic or otherwise undesirable for pesticidal use. Such salts may be derived from a variety of organic and inorganic counter-ions known in the art. Examples of such salts include, but are not limited to, alkali metal or alkaline earth metal salts and, particularly, calcium, magnesium, ammonium, sodium, lithium, zinc, potassium, and iron salts.

As used herein, the term "phenyl" means $-C_6H_5$. A phenyl group can be unsubstituted or substituted with one, two, three, four, five, or six suitable substituents.

As used herein, the term "purified" means that when isolated, the isolate contains at least 80%, at least 90%, at least 95%, at least 98%, or at least 99% of a compound described herein by weight of the isolate.

As used herein, the term "solution/suspension" means a liquid composition wherein a first portion of the active agent is present in solution and a second portion of the active agent is present in particulate form, in suspension in a liquid matrix.

As used herein, the phrase "suitable substituent" or "substituent" means a group that does not nullify the synthetic, pesticidal or pharmaceutical utility of the compounds described herein or the intermediates useful for preparing them. Examples of suitable substituents include, but are not limited to: $C_1$-$C_6$alkyl (e.g., $-CH_3$), $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, $-CN$, $-OH$, oxo, halo (e.g., $-F$), haloalkoxy (e.g., $-OCF_3$), haloalkyl (e.g., $-CF_3$), $-NO_2$, $-CO_2H$, $-NH_2$, $-NH(C_1$-$C_8$alkyl), $-N(C_1$-$C_8$alkyl)$_2$, $-NH(C_6$aryl), $-N(C_5$-$C_6$aryl)$_2$, $-CHO$, $-CO(C_1$-$C_6$alkyl), $-CO((C_5$-$C_6)$aryl), $-CO_2((C_1$-$C_6)$alkyl), and $-CO_2((C_5$-$C_6)$aryl). One of skill in art can readily choose a suitable substituent based on the stability, and pesticidal, pharmacological, or synthetic activity of the compounds described herein.

As used herein, the term "halo" means halogen groups including, but not limited to fluoro, chloro, bromo, and iodo.

As used herein, the term "haloalkoxy" means an $-O$-haloalkyl group. An example of an haloalkoxy group is $OCF_3$.

As used herein, the term "haloalkyl" means a $C_{1-6}$alkyl group having one or more halogen substituents. Examples of haloalkyl groups include, but are not limited to, $CF_3$, $C_2F_5$, $CH_2F$, $CHF_2$, $CCl_3$, $CHCl_2$, $CH_2CF_3$, and the like.

As used herein, the terms "controlling a pest" or "pest control" refers to the regulation or management of a pest including, but are not limited to, killing, poisoning, arresting reproduction of, and repelling the pest.

At various places in the present specification, substituents of compounds may be disclosed in groups or in ranges. It is specifically intended that embodiments include each and every individual subcombination of the members of such groups and ranges. For example, the term "$C_{1-6}$alkyl" is specifically intended to individually disclose methyl, ethyl, propyl, butyl, pentyl, and hexyl, including all regioisomers thereof.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

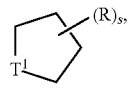

then it is understood that substituent R can occur s number of times on the ring, and R can be a different moiety at each occurrence. Further, in the above example, where the variable $T^1$ is defined to include hydrogens, such as when $T^1$ is $CH_2$, NH, etc., any H can be replaced with a substituent.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

It is understood that the present disclosure encompasses the use, where applicable, of stereoisomers, diastereomers, and optical stereoisomers of the compounds of the disclosure, as well as mixtures thereof. Additionally, it is understood that stereoisomers, diastereomers, and optical stereoisomers of the compounds of the disclosure, and mixtures thereof, are within the scope of the disclosure. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the disclosure unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds are also included within the scope of the disclosure and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, chiral HPLC, fractional recrystallization using a chiral resolving acid, which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti-arrangement of the two-carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

Embodiments of various compounds and salts thereof are provided. Where a variable is not specifically recited, the variable can be any option described herein, except as otherwise noted or dictated by context.

Compounds of the Disclosure

In one aspect, the present disclosure provides compounds according to Formula (I):

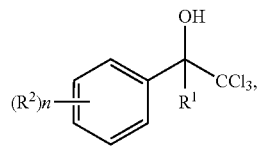

or a pesticidally acceptable salt thereof, wherein:
$R^1$ is selected from —H and —CH$_3$;
$R^2$ is independently at each occurrence selected from —F, —OCF$_3$, and —CF$_3$;
n is an integer from 1 to 5

In one aspect, the present disclosure provides compounds according to Formula (I):

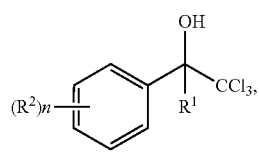

or a pesticidally acceptable salt thereof,
wherein:
$R^1$ is selected from —H and —CH$_3$;
$R^2$ is independently at each occurrence selected from —F, —OCF$_3$, and —CF$_3$;
n is an integer from 1 to 5, and
wherein when $R^1$ is H and n is 1, $R^2$ is not p-F, p-OCF$_3$, or p-CF$_3$;
wherein when $R^1$ is H and n is 2, $R^2$ is not p-F and m-F, and
wherein when $R^1$ is H and n is 5, $R^2$ is not —F at each occurrence.

In another aspect, the present disclosure provides compounds according to Formula (I):

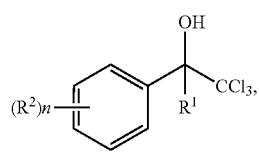

or a pesticidally acceptable salt thereof, wherein:
$R^1$ is selected from —H and —CH$_3$;
$R^2$ is independently at each occurrence selected from —F, —OCF$_3$, and —CF$_3$;

n is an integer from 1 to 5,
with the proviso that the compound according to Formula (I) is not:

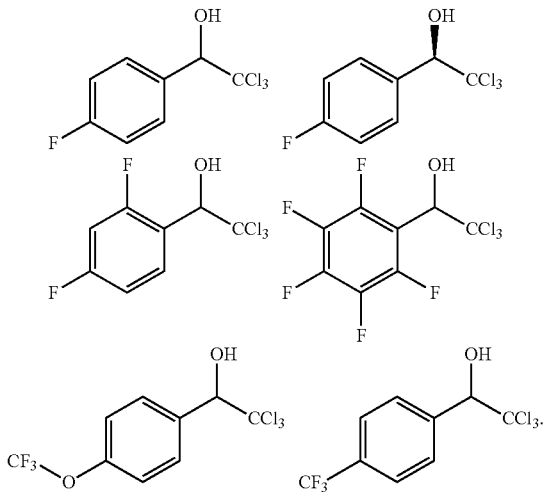

In some embodiments, the disclosure is directed to compounds of Formula (I) as described above.

In some embodiments, the disclosure is directed to a pesticidally acceptable salt of compounds of Formula (I) as described above.

In some embodiments, the disclosure is directed to compounds of Formula (I) with the proviso that wherein when $R^1$ is H and n is 1, $R^2$ is not p-F, p-OCF$_3$, or p-CF$_3$; wherein when $R^1$ is H and n is 2, $R^2$ is not p-F and m-F, and wherein when $R^1$ is H and n is 5, $R^2$ is not —F at each occurrence In some embodiments, the disclosure is directed to compounds of Formula (I) with the proviso that the compound according to Formula (I) is not:

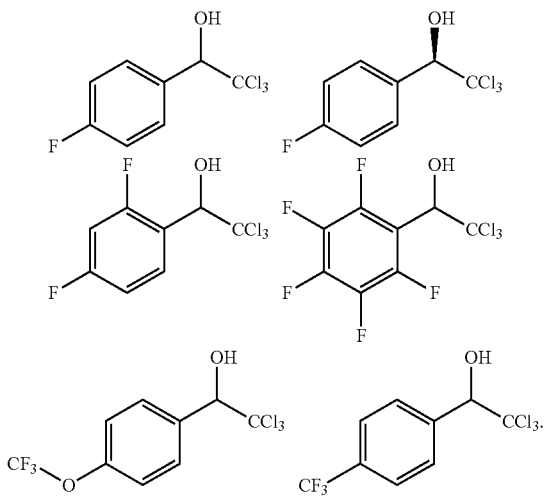

In some embodiments, $R^1$ is selected from —H and —CH$_3$. In some embodiments, $R^1$ is —H. In some embodiments, $R^1$ is —CH$_3$.

In some embodiments, $R^2$ is independently at each occurrence selected from —F, —OCF$_3$, and —CF$_3$. In some embodiments, $R^2$ is independently at each occurrence —F.

In some embodiments, $R^2$ is independently at each occurrence —OCF$_3$. In some embodiments, $R^2$ is independently at each occurrence —CF$_3$.

In some embodiments, n is an integer from 1 to 5. In some embodiments, n is an integer from 1 to 4. In some embodiments, n is an integer from 1 to 3. In some embodiments, n is an integer from 1 to 2. In some embodiments, n is an integer from 2 to 5. In some embodiments, n is an integer from 2 to 4. In some embodiments, n is an integer from 2 to 3. In some embodiments, n is an integer from 3 to 5. In some embodiments, n is an integer from 3 to 4. In some embodiments, n is 1. In some embodiments, n is 2. In some embodiments, n is 3. In some embodiments, n is 4. In some embodiments, n is 5.

In some embodiments, when $R^1$ is H and n is 1, $R^2$ is not p-F, p-OCF$_3$, or p-CF$_3$. In some embodiments, when $R^1$ is H and n is 1, $R^2$ is not p-F or p-CF$_3$. In some embodiments, when $R^1$ is H and n is 1, $R^2$ is not p-OCF$_3$, or p-CF$_3$. In some embodiments, when $R^1$ is H and n is 1, $R^2$ is not p-F or p-OCF$_3$. In some embodiments, when $R^1$ is H and n is 1, $R^2$ is not p-F. In some embodiments, when $R^1$ is H and n is 1, $R^2$ is not p-OCF$_3$. In some embodiments, when $R^1$ is H and n is 1, $R^2$ is not p-CF$_3$.

In some embodiments, when $R^1$ is H and n is 2, $R^2$ is not p-F or m-F. In some embodiments, when $R^1$ is H and n is 2, $R^2$ is not p-F. In some embodiments, when $R^1$ is H and n is 2, $R^2$ is not m-F.

In some embodiments, when $R^1$ is H and n is 5, $R^2$ is not —F at each occurrence.

In some embodiments, compounds are selected from the group consisting of:

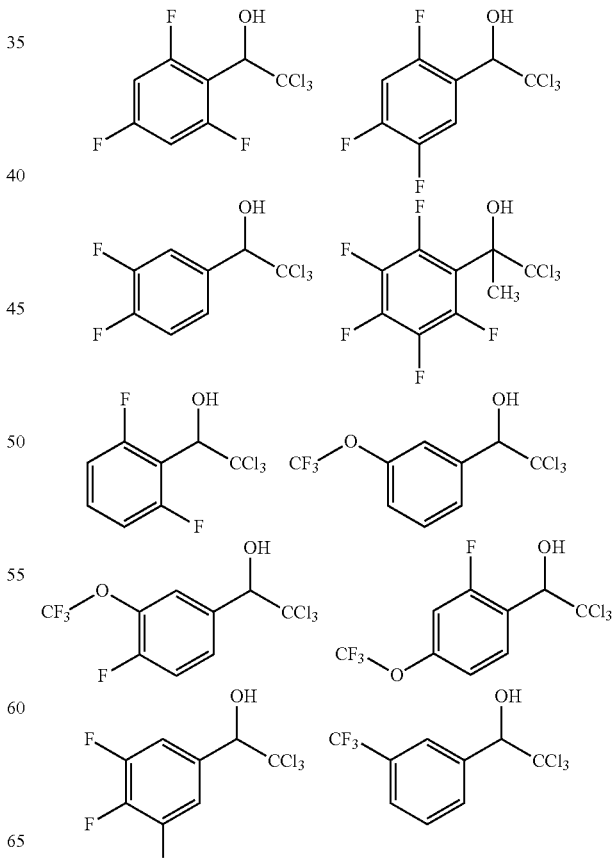

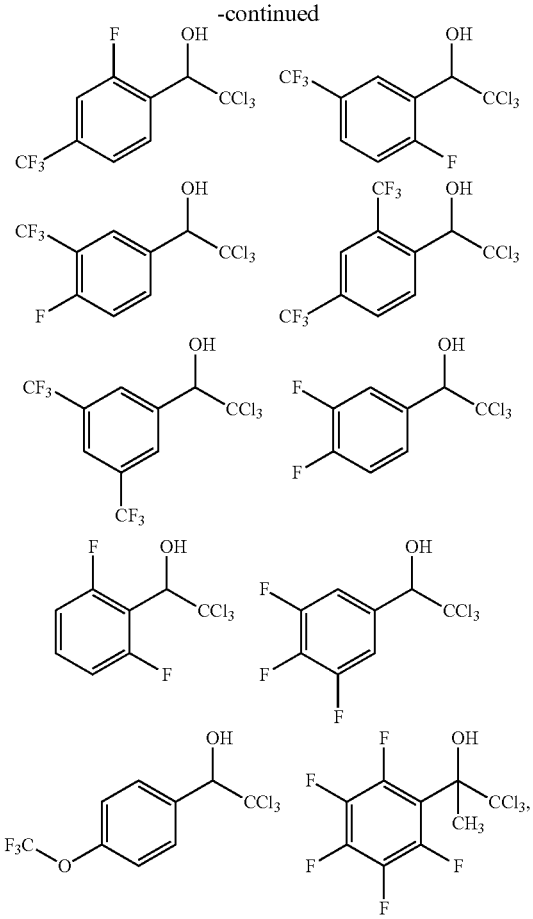

or a pesticidally acceptable salt thereof.

In some embodiments, compounds of the present disclosure are selected from the group consisting of:

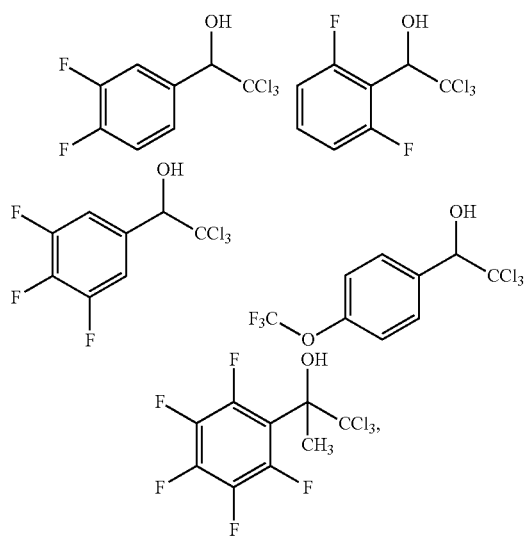

or a pesticidally acceptable salt thereof.

In some embodiments, the disclosure is directed to a compound as described herein, wherein a hydrogen is replaced with a deuterium. In some embodiments, the compound has a formula of Formula (I), wherein the variables are as defined herein.

In some embodiments, the disclosure is directed to pesticidal compositions comprising a compound as described herein and a pesticidally acceptable carrier.

In some embodiments, the disclosure is directed to pesticidal compositions comprising a compound as described herein, wherein the composition comprises a racemic mixture of the compound.

In some embodiments, the disclosure is directed to pesticidal compositions comprising a compound as described herein, wherein the composition comprises an enantioenriched mixture of the compound. In some embodiments, the pesticidal composition comprises an enantiomeric excess of at least, or about, 80, 85, 90, 91, 92, 93, 94, 95, 96, 97, 98, 99% of a specific enantiomer of a compound provided herein, such as the R or the S enantiomer. In some embodiments, the pesticidal composition comprises an enantiomeric excess of at least, or about, 80, 85, 90, 91, 92, 93, 94, 95, 96, 97, 98, 99% of a specific enantiomer of a compound provided herein, such as the R enantiomer. In some embodiments, the enantiomeric excess of R enantiomer is at least, or about 80%. In some embodiments, the enantiomeric excess of R enantiomer is at least, or about 85%. In some embodiments, the enantiomeric excess of R enantiomer is at least, or about 90%. In some embodiments, the enantiomeric excess of R enantiomer is at least, or about 91%. In some embodiments, the enantiomeric excess of R enantiomer is at least, or about 92%. In some embodiments, the enantiomeric excess of R enantiomer is at least, or about 93%. In some embodiments, the enantiomeric excess of R enantiomer is at least, or about 94%. In some embodiments, the enantiomeric excess of R enantiomer is at least, or about 95%. In some embodiments, the enantiomeric excess of R enantiomer is at least, or about 96%. In some embodiments, the enantiomeric excess of R enantiomer is at least, or about 97%. In some embodiments, the enantiomeric excess of R enantiomer is at least, or about 98%. In some embodiments, the enantiomeric excess of R enantiomer is at least, or about 99%.

In one embodiment, the disclosure is directed to the use of (RS)-MFTE or (RS)-PFTE as a pesticide. In one embodiment, the disclosure is directed to the use of R-MFTE or R-PFTE as a pesticide:

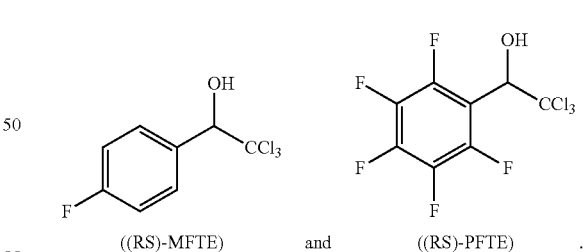

((RS)-MFTE)    and    ((RS)-PFTE)

In some embodiments, the disclosure is directed to pesticidal compositions comprising a compound as described herein in combinations with one or more other pesticidally active substances, such as, for example, insecticides, attractants, sterilants, nematicides, acaricides, fungicides, herbicides, and with safeners, fertilizers, or growth regulators other than the compound described herein. The combinations may be part of the same formulation, or may be administered separately or sequentially to the locus.

In some embodiments, the disclosure is directed to pesticidal compositions comprising a compound as described herein in combinations with a pesticidally acceptable carrier. In some embodiments, the combination comprising a compound of the present disclosure and one or more other pesticidally active substances other than the compounds described herein.

In some embodiments, the disclosure is directed to methods of preparing an enantiomer of a compound according to Formula (II):

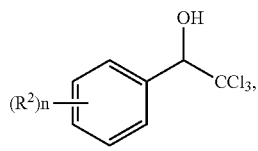
(II)

wherein the methods comprise the steps of:
a) reacting a compound of Formula (IIa):

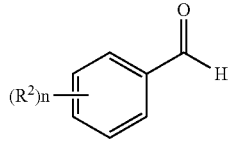
(IIa)

with trichloroacetic acid and sodium trichloroacetate to give a racemic mixture of the compound of Formula (II).
b) reacting the racemic mixture of the compound of Formula (II) with Dess-Martin reagent, thereby affording a compound of Formula (IIb):

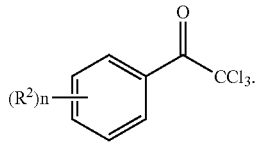
(IIb)

c) reacting the compound of Formula (IIb) with (R) oxazaborolidine or (S) oxazaborolidine.
d) reacting the mixture of step c) with catechol borane, and
e) isolating the enantiomer of the compound according to Formula (II).

In some embodiments, the disclosure is directed to methods of controlling a pest comprising applying to the pest or its locus a compound according to formula (I):

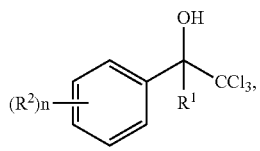
(I)

or a pesticidal composition thereof,
or a pesticidally acceptable salt thereof, wherein $R^1$ is selected from —H and —CH$_3$; $R^2$ is independently at each occurrence selected from —F, —OCF$_3$, and —CF$_3$; n is an integer from 1 to 5.

In some embodiments, the methods of controlling a pest comprising applying to the pest or its locus a compound according to formula

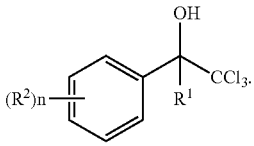
(I)

In some embodiments, the methods of controlling a pest comprising applying to the pest or its locus or a pesticidal composition comprising at least one compound of

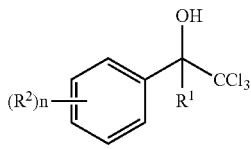

as described herein. In some embodiments, the methods of controlling a pest comprising applying to the pest or its locus a pesticidally acceptable salt or solvate of a compound of

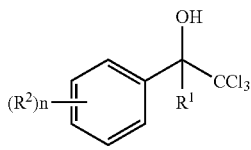

as described herein. In some embodiments, $R^1$ is selected from —H and —CH$_3$. In some embodiments, $R^1$ is —H. In some embodiments, $R^1$ is —CH$_3$. In some embodiments, $R^2$ is independently at each occurrence selected from —F, —OCF$_3$, and —CF$_3$. In some embodiments, $R^2$ is independently at each occurrence —F. In some embodiments, $R^2$ is independently at each occurrence —OCF$_3$. In some embodiments, $R^2$ is independently at each occurrence —CF$_3$. In some embodiments, n is an integer from 1 to 5. In some embodiments, n is an integer from 1 to 4. In some embodiments, n is an integer from 1 to 3. In some embodiments, n is an integer from 1 to 2. In some embodiments, n is an integer from 2 to 5. In some embodiments, n is an integer from 2 to 4. In some embodiments, n is an integer from 2 to 3. In some embodiments, n is an integer from 3 to 5. In some embodiments, n is an integer from 3 to 4. In some embodiments, n is 1. In some embodiments, n is 2. In some embodiments, n is 3. In some embodiments, n is 4. In some embodiments, n is 5. In some embodiments, when $R^1$ is H and n is 1, $R^2$ is not p-F. In some embodiments, the compound has an insecticidal knock down speed of at least twice as active, at least 3 times as active, at least 4 times as active, at least 5 times as active, at least 6 times as active, at least 7 times as active, at least 8 times as active, or at least 9 times as active as DDT. In some embodiments, the compound has an insecticidal knock down speed of at least twice as active, at least 3 times as active, at least 4 times as active, at least 5 times as active, at least 6 times as active, at least 7 times as active, at least 8 times as active, or at least 9 times as active as DDT. In some embodiments, the compound has an insecticidal knock down speed of at least twice as active, at least 3 times as active, at least 4 times as active, at least 5 times as active, at least 6 times as active, at least 7 times as active, at least 8 times as active, or at least 9 times as active as DDT. In some embodiments, the compound has an insecticidal knock down speed of at least twice as active, at least 3 times as active, at least 4 times as active, at least 5 times as active, at least 6 times as active, at least 7 times as active, at least 8 times as active, or at least 9 times as active as DDT. In some embodiments, the compound has an insecticidal knock down speed of at least twice as active, at least 3 times as active, at least 4 times as active, at least 5 times as active, at least 6 times as active, at least 7 times as active, at least 8 times as active, or at least 9 times as active as DDT. In some embodiments, the compound has an insecticidal knock down speed of at least twice as active, at least 3 times as active, at least 4 times as active, at least 5 times as active, at least 6 times as active, at least 7 times as active, at least 8 times as active, or at least 9 times as active as DDT. In some embodiments, the compound has an insecticidal knock down speed of at least twice as active as DDT. In some embodiments, the compound has an insecticidal knock down speed of at least 3 time as active as DDT. In some embodiments, the compound has an insecticidal knock down speed of at least 4 time as active as DDT. In some embodiments, the compound has an insecticidal knock down speed of at least 5 time as active as DDT. In some embodiments, the compound has an insecticidal knock down speed of at least 6 time as active as DDT. In some embodiments, the compound has an insecticidal knock down speed of at least 7 time as active as DDT. In some embodiments, the compound has an insecticidal knock down speed of at least 8 time as active as DDT. In some embodiments, the compound has an insecticidal knock down speed of at least 9 time as active as DDT.

In some embodiments, the disclosure is directed to methods of controlling a pest as described herein, wherein the pest is an insect. In some embodiments, the insect is selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas (indoors & outdoors), flea beetles, flies, flesh flies, fruit flies, fungus gnats (sciarid flies), gnats, grasshoppers, green bottle flies, greenstriped mapleworms, ground beetles, gypsy moths (larvae), hide beetles, house flies, hornets, horseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, redhumped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellownecked caterpillar, wasps, and webworms.

Although the compounds described herein may be shown with specific stereochemistries around certain atoms, such as R or S, the compounds can also be made in the opposite orientation or in a racemic mixture. Such isomers or racemic mixtures are encompassed by the present disclosure.

In some embodiments, the present disclosure provides pesticidal compositions comprising a compound or pesticidally salt thereof of any compound described herein.

The compounds described herein can be made according to the methods described herein and in the examples. The methods described herein can be adapted based upon the compounds desired and described herein. In some embodiments, the method is made according to the following schemes, wherein the substituents as shown and described herein and would be apparent to one of skill in the art based upon the present disclosure. In some embodiments, this method can be used to make one or more compounds as described herein and will be apparent to one of skill in the art which compounds can be made according to the methods described herein.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquatemium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the compounds are solubilized at least in part by an acceptable solubilizing agent. Certain acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

In some embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

The present disclosure also provides pesticidal packs or kits comprising one or more containers filled with one or more compounds described herein. Optionally associated with such container(s) can be a notice in the form prescribed by a governmental agency regulating the manufacture, use or sale of pesticidal or biological products, which notice reflects approval by the agency of manufacture, use or sale for treating a pest condition described herein. In some embodiments, the kit contains more than one compound described herein.

The present disclosure also provides the following non-limiting embodiments:

1. A compound according to Formula (I):

(I)

or a pesticidally acceptable salt thereof, wherein:
$R^1$ is selected from —H and —CH$_3$;
$R^2$ is independently at each occurrence selected from —F, —OCF$_3$, and —CF$_3$;
n is an integer from 1 to 5, and
wherein when $R^1$ is H and n is 1, $R^2$ is not p-F, p-OCF$_3$, or p-CF$_3$;
wherein when $R^1$ is H and n is 2, $R^2$ is not p-F and m-F, and
wherein when $R^1$ is H and n is 5, $R^2$ is not —F at each occurrence.

2. A compound according to Formula (I):

(I)

or a pesticidally acceptable salt thereof, wherein:
$R^1$ is selected from —H and —CH$_3$;
$R^2$ is independently at each occurrence selected from —F, —OCF$_3$, and —CF$_3$;
n is an integer from 1 to 5,
with the proviso that the compound according to Formula (I) is not:

3. The compound according to embodiments 1 or 2, wherein $R^1$ is H.
4. The compound according to embodiments 1 or 2, wherein $R^1$ is —CH$_3$.
5. The compound according to any of embodiments 1-4, wherein $R^2$ is —F.
6. The compound according to any of embodiments 1-4, wherein $R^2$ is —OCF$_3$.
7. The compound according to any of embodiments 1-4, wherein $R^2$ is —CF$_3$.
8. A compound selected from the group consisting of:

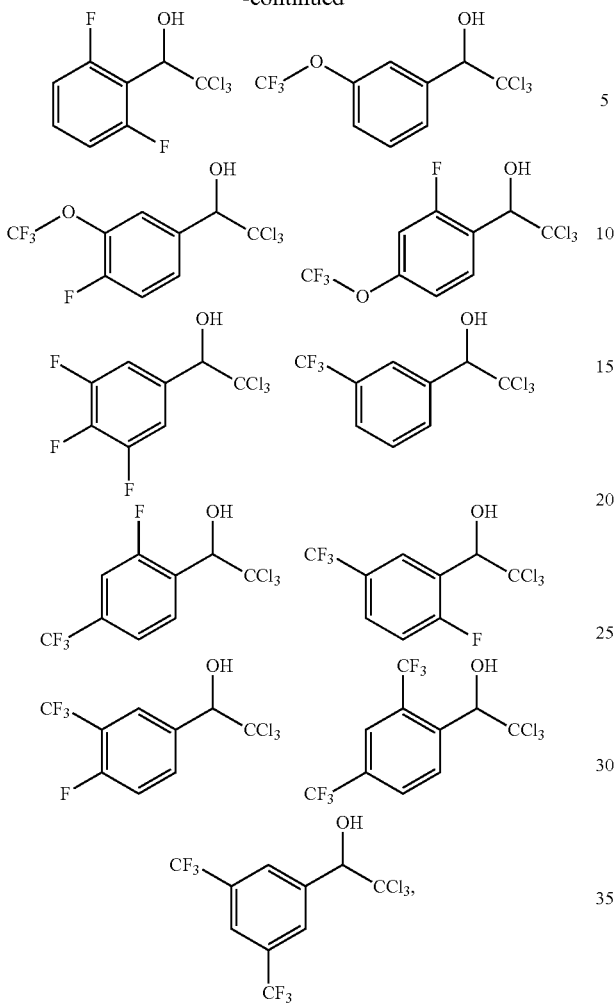

or a pesticidally acceptable salt thereof.

9. A pesticidal composition comprising the compound according to any of embodiments 1-8, wherein the composition comprises a racemic mixture of the compound.

10. The pesticidal composition comprising the compound according to any of embodiments 1-8, wherein the composition comprises an enantioenriched mixture of the compound.

11. The pesticidal composition comprising the compound according to any of embodiments 1-8, wherein the compound is present in an enantiomeric excess of about 90% or more.

12. A method of preparing an enantiomer of a compound according to Formula (II):

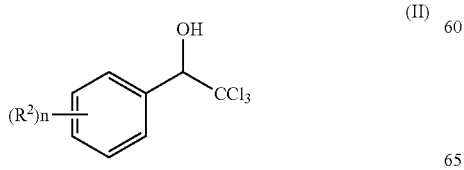

comprising the steps of:
a) reacting a compound of Formula (IIa):

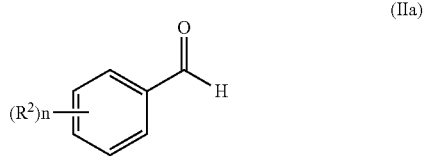

with trichloroacetic acid and sodium trichloroacetate to give a racemic mixture of the compound of Formula (II);
b) reacting the racemic mixture of the compound of Formula (II) with Dess-Martin reagent, thereby affording a compound of Formula (IIb):

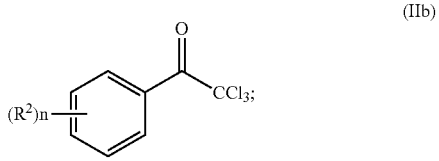

c) reacting the compound of Formula (IIb) with (R) oxazaborolidine or (S) oxazaborolidine;
d) reacting the mixture of step c) with catechol borane, and
e) isolating the enantiomer of the compound according to Formula (II).

13. A method of controlling a pest comprising applying to the pest or its locus a compound according to formula (I):

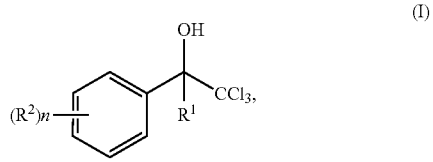

or a pesticidally acceptable salt thereof, wherein:
$R^1$ is selected from —H and —$CH_3$;
$R^2$ is independently at each occurrence selected from —F, —$OCF_3$, and —$CF_3$;
n is an integer from 1 to 5;
wherein the compound has an insecticidal knock down speed of at least twice as active, at least 3 times as active, at least 4 times as active, at least 5 times as active, at least 6 times as active, at least 7 times as active, at least 8 times as active, or at least 9 times as active as DDT.

14. A method of controlling a pest comprising applying to the pest or its locus a compound according to Formula (I):

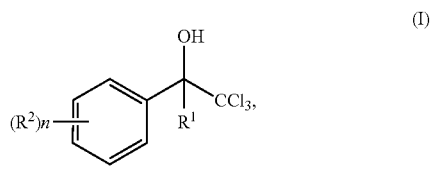

or a pesticidally acceptable salt thereof, wherein:
$R^1$ is selected from —H and —$CH_3$;
$R^2$ is independently at each occurrence selected from —F, —$OCF_3$, and —$CF_3$;
n is an integer from 1 to 5,
wherein when $R^1$ is H, and n is 1, $R^2$ is not p-F.

15. The method according to embodiments 13 or 14, wherein $R^1$ is —H.

16. The method according to embodiments 13 or 14, wherein $R^1$ is —$CH_3$

17. The method according to any one of embodiments 13-16, wherein $R^2$ is —F.

18. The method according to any one of embodiments 13-16, wherein $R^2$ is —$OCF_3$.

19. The method according to any one of embodiments 13-16, wherein $R^2$ is —$CF_3$.

20. A method of controlling a pest comprising applying to the pest or its locus the compound according to any one of embodiments 1-8, or a pesticidal composition according to any one of embodiments 9-11.

21. The method of any one of the preceding embodiments, wherein the pest is an insect.

22. The method of embodiment 21, wherein the insect is selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas (indoors & outdoors), flea beetles, flies, flesh flies, fruit flies, fungus gnats (sciarid flies), gnats, grasshoppers, green bottle flies, greenstriped mapleworms, ground beetles, gypsy moths (larvae), hide beetles, house flies, hornets, horseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, redhumped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellownecked caterpillar, wasps, and webworms.

EXAMPLES

The following examples illustrate specific aspects of the instant description. The examples should not be construed as limiting, as the examples merely provide specific understanding and practice of the embodiments and their various aspects Example 1: Polymorphic Forms DFDT and MFDT This example demonstrates that newly discovered solid-state forms of DFDT and its chiral monofluoro analog MFDT (1,1,1-trichloro-2,2-(4-chlorophenyl)-(4-fluorophenyl)-ethane; FIG. 1A) act much more rapidly than DDT against *Drosophila* as well as *Anopheles quadrimaculatus*, a vector for malaria, and *Aedes aegypti*, a vector for Zika virus, yellow fever, dengue, and chikungunya, as shown in FIG. 1. FIG. 1A illustrates molecular structures of DFDT and MFDT. FIG. 1B illustrates that DFDT-I single crystal (space group, P21/c) is isostructural with (RS)-MFDT-II single crystal. FIG. 1C illustrates DFDT-II single crystal ($P2_1$/c). FIG. 1D illustrates (RS)-MFDT-I (P). FIG. 1E illustrates (R)-MFDT single crystal and FIG. 1F (S)-MFDT single crystal ($P2_1$). FIG. 1G illustrates (RS)-MFDT-III single crystal (Pbca). FIG. 1H illustrates broad powder X-ray diffraction (PXRD) halos observed for amorphous forms. Atom colors: hydrogen (white); carbon (gray); fluorine (magenta); chlorine (green).

DFDT and MFDT were synthesized from trichloroacetate and para-fluorobenzaldehyde to give 1-(4-fluorophenyl)-2,2,2-trichloroethanol. Subsequent reaction with fluorobenzene or chlorobenzene afforded DFDT and MFDT, respectively. Two polymorphic crystalline forms of DFDT (DFDT-I, -II) and three polymorphic forms of racemic MFDT ((RS)-MFDT-I, -II, -III) were discovered. DFDT-I single crystals could be obtained from a variety of solvents and DFDT-II single crystals from diethyl ether. (RS)-MFDT-I could be crystallized from a variety of solvents. The (R)- and (S)-MFDT enantiomers were resolved by chromatography on a chiral stationary phase, and single crystals were grown from a variety of solvents. Curiously, single crystals of (RS)-MFDT-II and -III were obtained by crystallization from the melt at >30° C. and 25° C., respectively, using seed crystals of either the R or S isomers. These crystalline forms, six total, were characterized by single crystal X-ray diffraction (FIG. 1). The melting points of DFDT-I and II were similar ($T_m$=40° C. and 39° C., respectively, but microcrystalline DFDT-II slowly transformed to DFDT-I at room temperature, indicating that the latter is more thermodynamically stable. (RS)-MFDT-II and III microcrystals slowly transformed to (RS)-MFDT-I at room temperature, although III transformed much more rapidly. The apparent thermodynamic stabilities of crystalline MFDT racemate parallel their melting points, $T_m$: RS-I (62° C.)>RS-II (54° C.)>RS-III (35° C.). Collectively, this is strong evidence (RS)-MFDT-III is less stable than its Form II at room temperature, especially given the low melting point of Form III. The $T_m$ of the enantiomorphs was 47° C. Amorphous DFDT (a-DFDT), prepared by supercooling melts or fine mist spraying of solutions, afforded broad X-ray scattering halos (FIG. 1H) and was stable for 25 days at room temperature. Amorphous resolved and racemic MFDT (a-(R)- and a-(S)-MFDT, and a-(RS)-MFDT, respectively; FIG. 1H) were stable for 10 days at room temperature. These observations contrast with a-DDT, which transformed to crystalline DDT Form I within 5 hours at room temperature. Notably, a-DFDT is stable for at least 120 days by addition of 10 wt % PEG 100 emulsifier, promising its use as a contact insecticide.

Example 2: Lethalities of Solid-State Forms of DFDT, MFDT and DDT for *Drosophila melanogaster*

Figure 2:
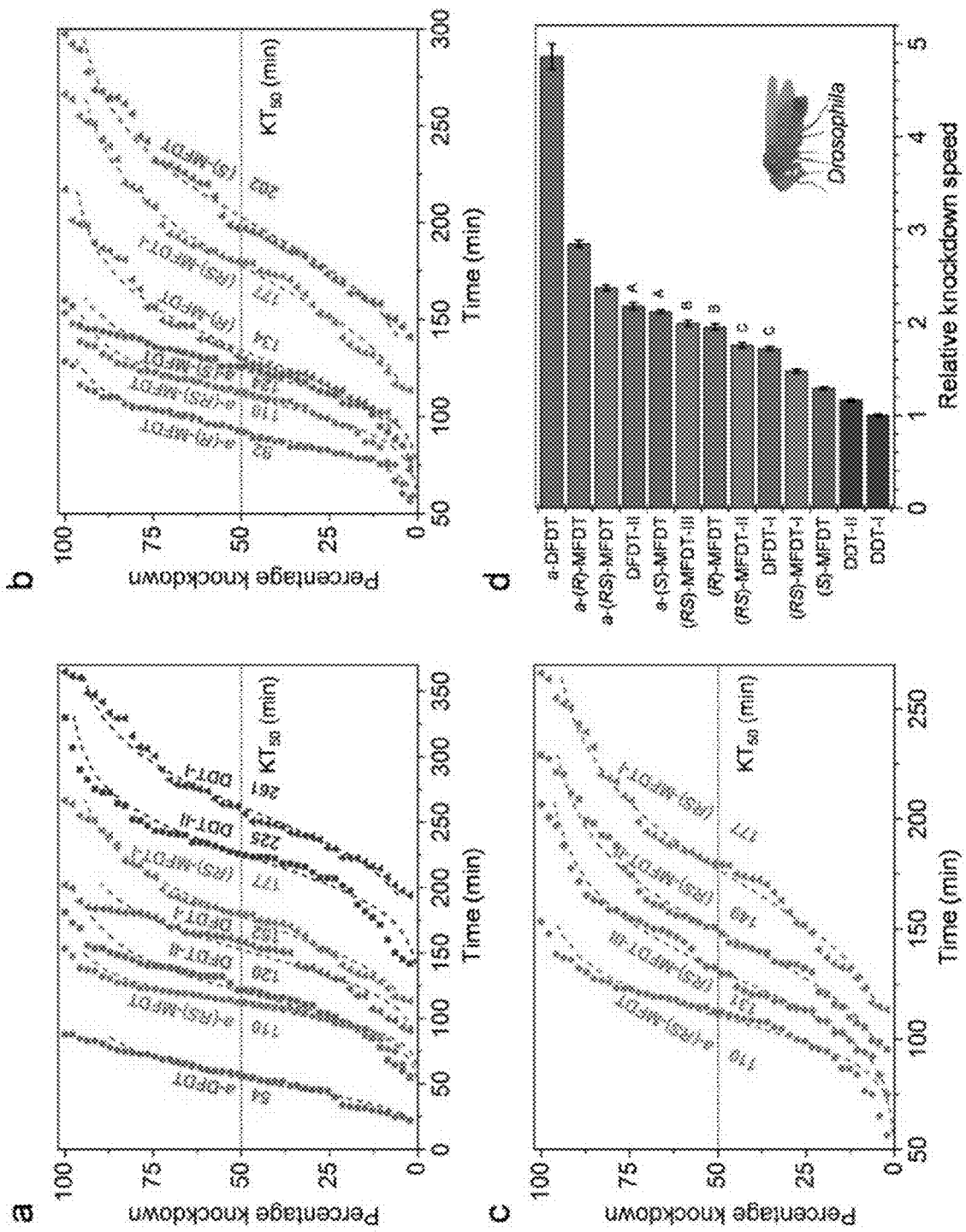
FIG. 2 illustrates lethalities of solid-state forms of DFDT, MFDT and DDT for *Drosophila melanogaster*.

This example demonstrates the lethalities of solid-state forms of DFDT, MFDT and DDT for *Drosophila melanogaster*. The results are as shown in FIG. 2. Each symbol of FIGS. 2A-C corresponds to one female. Dashed lines indicate logistic regression of knockdown-time curves. The median knockdown time for each curve is denoted by its intersection with the horizontal $KT_{50}$ marker. FIG. 2D illustrates comparison of the knockdown speeds (1/KT$_{50}$) relative to DDT I. Error bars represent 95% confidence intervals (CI). Values with the same letter have overlapping 95% CIs and differences are considered insignificant. Inset: Photo of a typical female fly.

Female *Drosophila melanogaster* were exposed to 2.0±0.1 mg of DFDT, MFDT and DDT separately, in their crystalline and amorphous forms. The insects were monitored with a video camera until the entire population ceased to move. The videos then were analyzed to determine the knockdown times—a proxy for lethality—for each individual insect (Videos S1-S5). Like DDT, DFDT and MFDT induced hyperactivity followed by paralysis, and then death. KT$_{50}$ values, the times required for death of 50% of the insects, are the standard for assessing insecticide lethality (the lifetimes of individual insects differ because of the random nature of their contact with insecticide surfaces and varied susceptibility of a population). Here, the KT$_{50}$ values were calculated by logistic regression of knockdown-time curves. The KT$_{50}$ values spanned the range of 261 min to 54 min, decreasing in the order DDT-I>DDT-II>(S)-MFDT>(RS)-MFDT-I>DFDT-I~(RS)-MFDT-II>(R)-MFDT~(RS)-MFDT-III>a-(S)-MFDT~DFDT-II>a-(RS)-MFDT>a-(R)-MFDT>a-DFDT (FIG. 2a-c). Knockdown speeds, reciprocals of KT$_{50}$ values, decreased in inverse order (FIG. 2d). The amorphous forms are always faster than their respective crystalline counterparts, with a-DFDT the fastest. The MFDT R forms, whether crystalline or amorphous, have higher knockdown speeds than their respective S forms suggesting enantioselectivity in uptake by the insect or neurotoxicity. Overall, the lethalities of the different solid forms of a given compound, as deduced from their knockdown speeds, were inversely correlated with their thermodynamic stability.

Example 3: Lethalities of Crystalline and Amorphous Forms of DFDT, (RS)-MFDT, and DDT for *Anopheles quadrimaculatus* and *Aedes aegypti*

Figure 3:
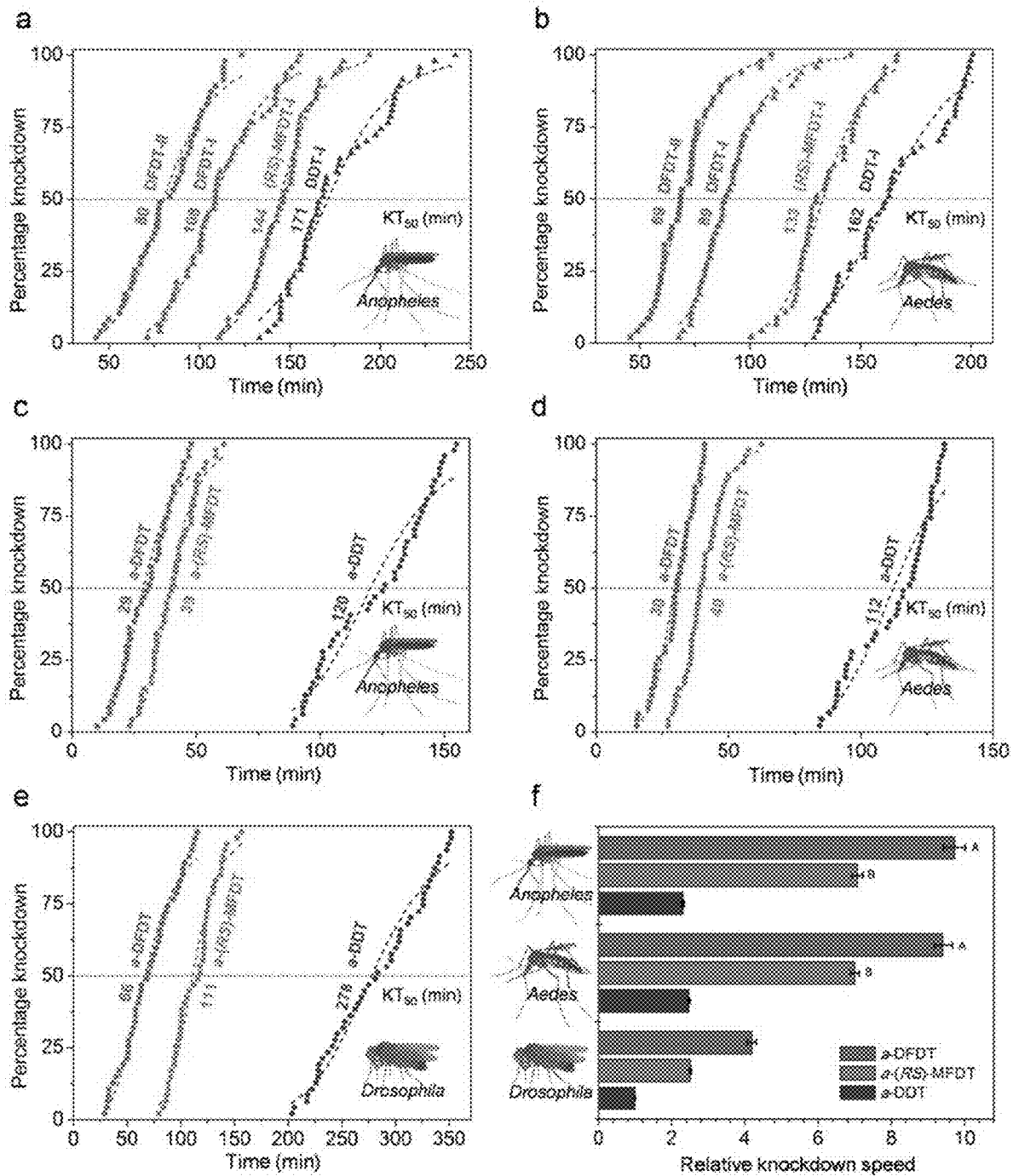
FIG. 3 illustrates lethalities of crystalline and amorphous forms of DFDT, (RS)-MFDT and DDT for *Anopheles quadrimaculatus* (a) and *Aedes aegypti* (b).

This example demonstrates the lethalities of crystalline and amorphous forms of DFDT, (RS)-MFDT and DDT for *Anopheles quadrimaculatus* (FIG. 3A) and *Aedes aegypti* (FIG. 3B). The results are as shown in FIG. 3. Each symbol corresponds to one female. Dashed lines indicate logistic regression of knockdown-time curves. The median knockdown time for each curve is denoted by its intersection with the horizontal KT$_{50}$ marker. FIG. 3F illustrates the relative knockdown speeds of amorphs. Error bars represent 95% confidence intervals (CI). Values with the same letter have overlapping 95% CIs and differences are considered insignificant. Insets: Photos of typical *Anopheles* and *Aedes* mosquito females.

Female *Anopheles* and *Aedes* mosquitoes exposed to 1.0±0.1 mg of various crystalline forms followed the same knockdown trend as *Drosophila*, see Example 2, with KT$_{50}$ values decreasing in the order DDT-I>(RS)-MFDT-I>DFDT-I>DFDT-II (FIGS. 3A and 3B). Given that DFDT and MFDT amorphs were more active than their crystalline forms against *Drosophila*, the lethalities of the amorphous forms were evaluated as well for *Anopheles* and *Aedes* mosquitoes. Female mosquitoes were introduced into petri dishes coated with 1.0±0.1 mg of the amorphous forms, and their motions recorded (Videos S8-S10). KT$_{50}$ values for a-DFDT and a-(RS)-MFDT against *Anopheles* were 29 and 39 minutes, and against *Aedes* were 30 and 40 minutes, respectively (FIGS. 3C and 3D). Corresponding KT$_{50}$ values for a-DDT were much larger (120 and 112 minutes). Accordingly, the knockdown speeds for a-DFDT and a-(RS)-MFDT are 4 and 3 times faster than a-DDT, respectively (FIG. 3F).

Example 4: Lethalities of Amorphous and Liquid Forms of Fluorine-Containing Compounds for *Drosophila melanogaster*

Figure 4:
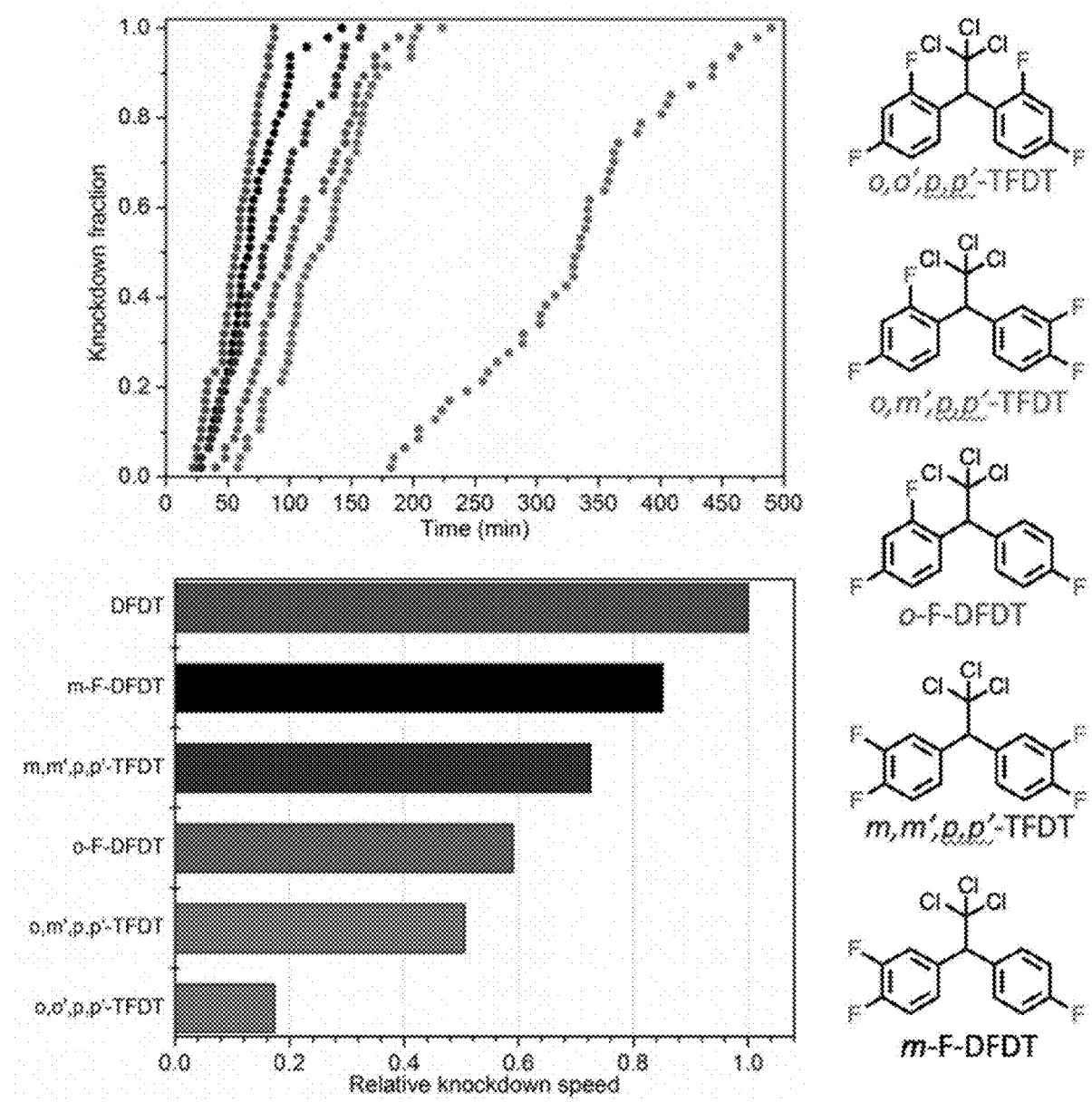
FIG. 4 illustrates the Lethalities of amorphous or liquidus forms of fluorine containing compounds for *Drosophila melanogaster*.

This example demonstrates the lethalities of amorphous and liquid forms of fluorine containing compounds depicted in FIG. 4 for *Drosophila melanogaster*. These fluorine-containing compounds are aromatic insecticides that resemble DFDT. Each of these compounds was tested against *Drosophila* and none of them is more effective than the historical compounds, DFDT. The test results are as shown in FIG. 4.

Example 5: Preparations of DFDT and Related Compounds

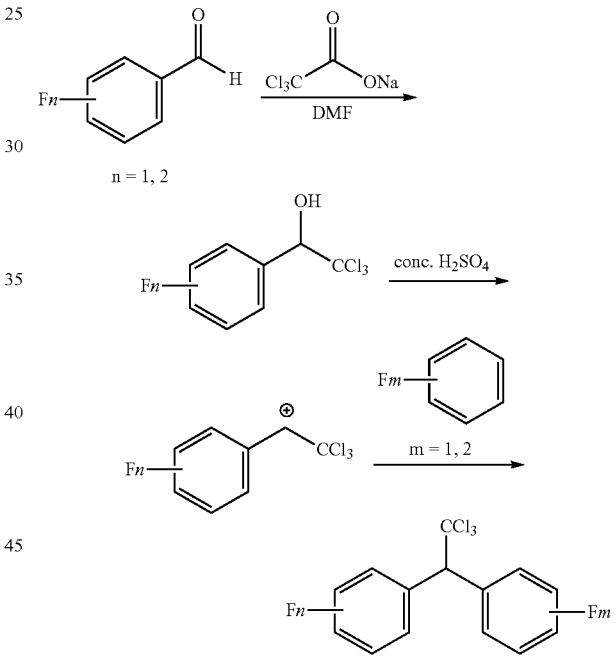

Scheme 1: synthetic route for the compounds according to the disclosure

This example describes the preparation of DFDT and related compounds as described herein. A synthetic route to the compounds of the present disclosure is shown in Scheme 1. The industrial synthesis of DFDT and DDT uses one step from chloral, a controlled substance, so a new synthetic route as shown in Scheme 1 has been developed.

Figure 5:
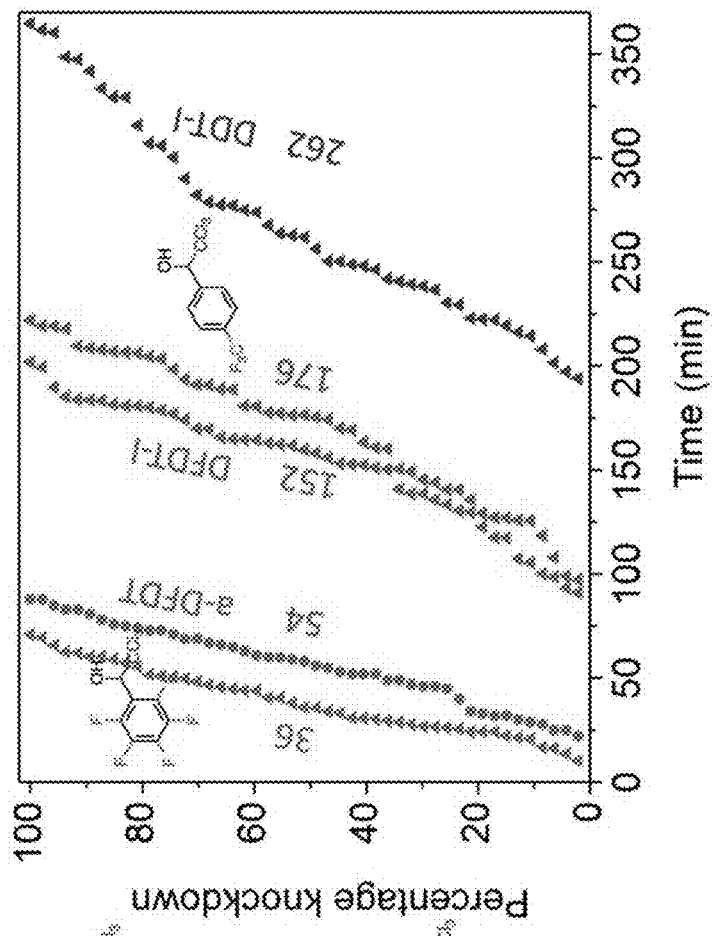
FIG. 5 illustrates the preparations of fluoroaryltrichloromethylethanols (FTEs) and propanols (FTPs).
Figure 5:
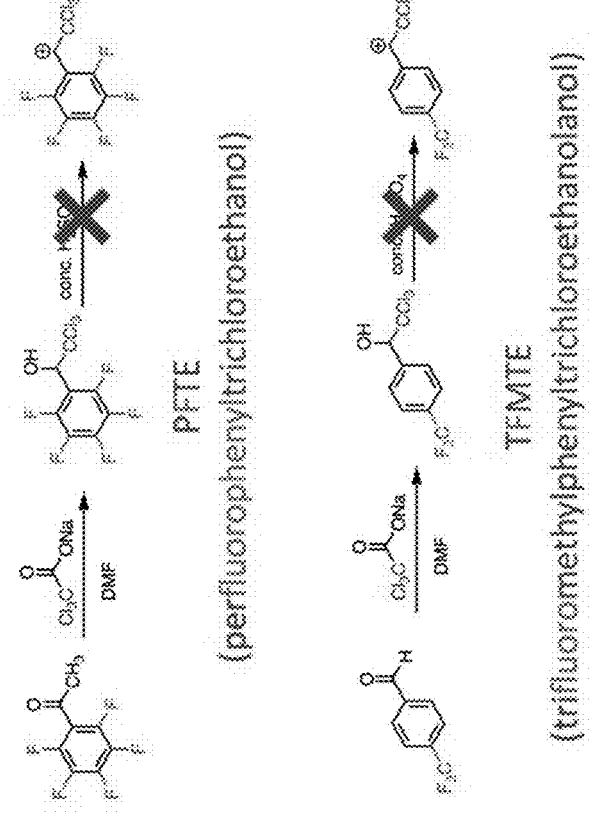

This procedure failed when very unstable carbocation intermediates were required. In this case, two alcohol intermediates were isolated: PFTE (perfluorophenyltrichloroethanol) and TFMTE (trifluoromethylphenyltrichloroethanol). These two alcohols showed unexpected and surprising insecticidal potential, as shown in FIG. 5. For example. *Drosophila* knockdown times for crystalline PFTE were smaller than amorphous DFDT. PFTE is a secondary alcohol and only resembles DDT in that it carries a trichloromethyl substituent. Therefore, there is every reason to believe that the mode of action is as different from DDT and DFDT. A second example, TFMTE, was faster than DDT Form I, but not as fast as PFTE.

Example 5: Preparation of Fluoroaryltrichloromethylethanols (FTEs) and Propanols (FTPs)

This example demonstrates that the synthetic procedure as shown in Scheme 2 had been used to prepare more than 30 analogs of PFTE and TFMTE (Scheme 2) for the preliminary study of structure-activity relationships (SAR). Given that the lethalities of compounds are strongly dependent on their solid-state forms, the physical state of each compound at room temperature was characterized and denoted in Scheme 2.

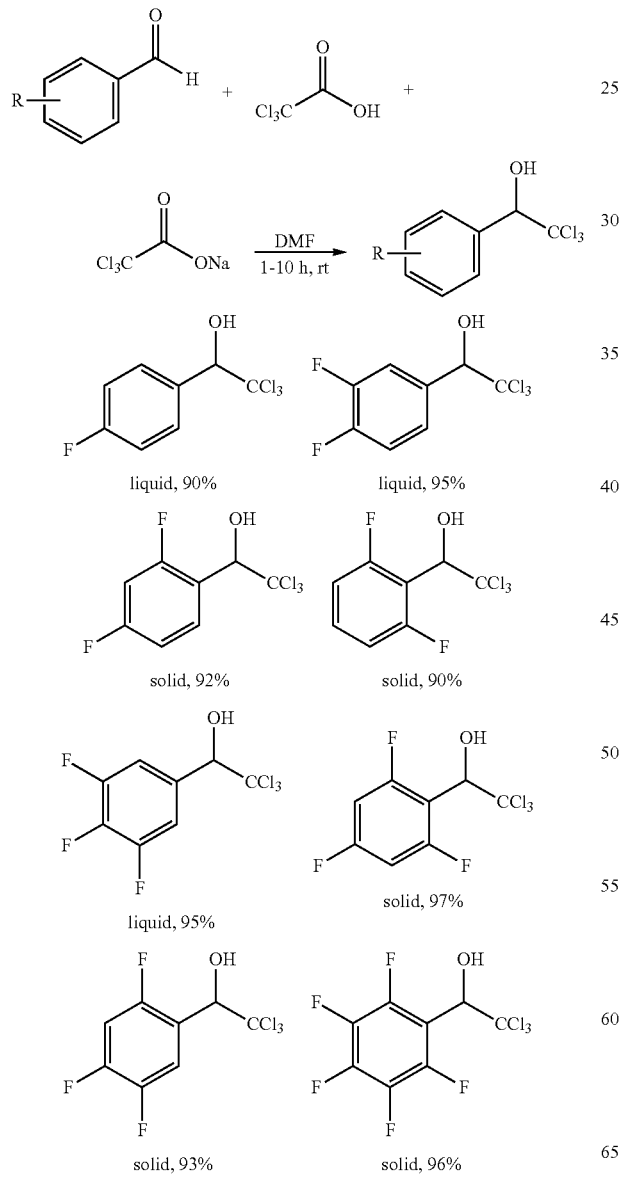

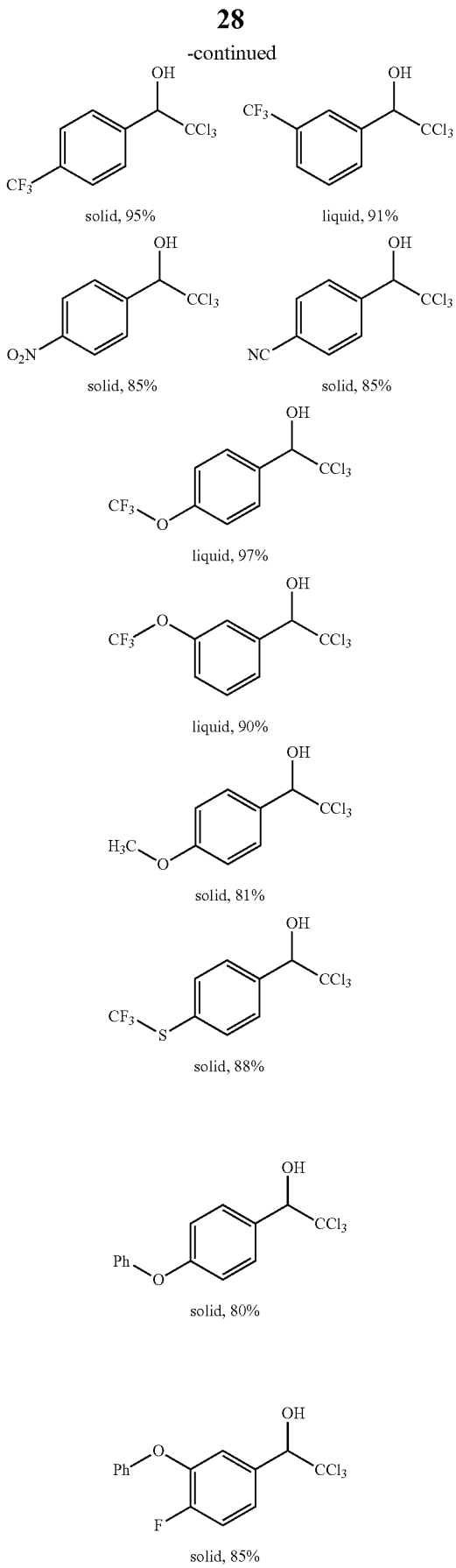

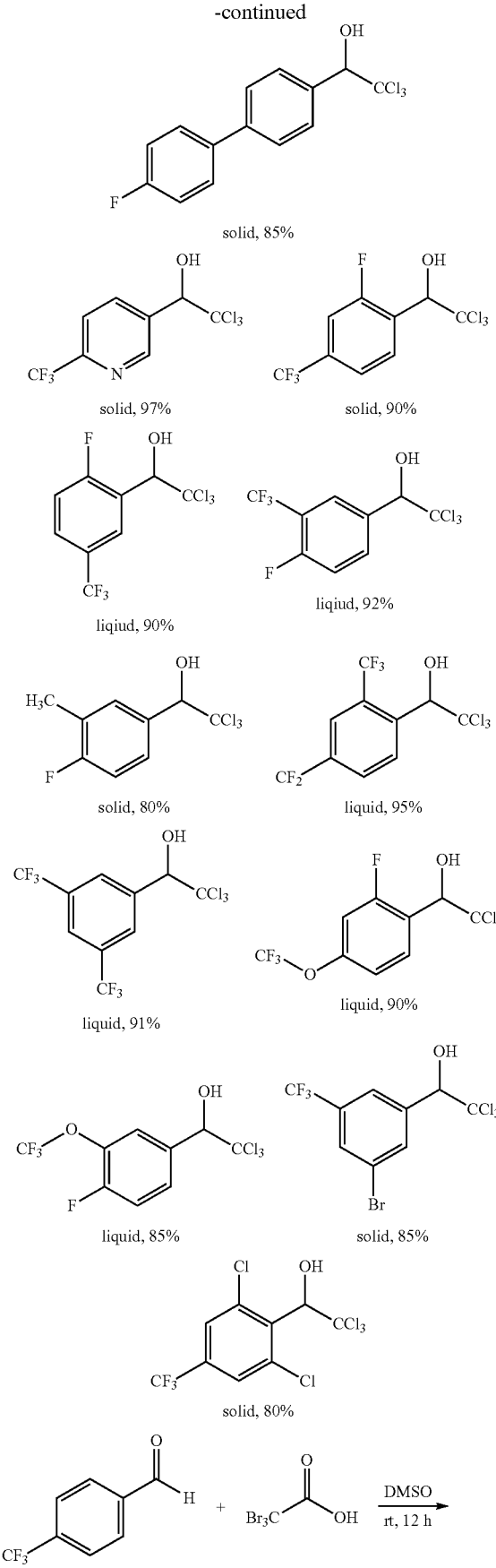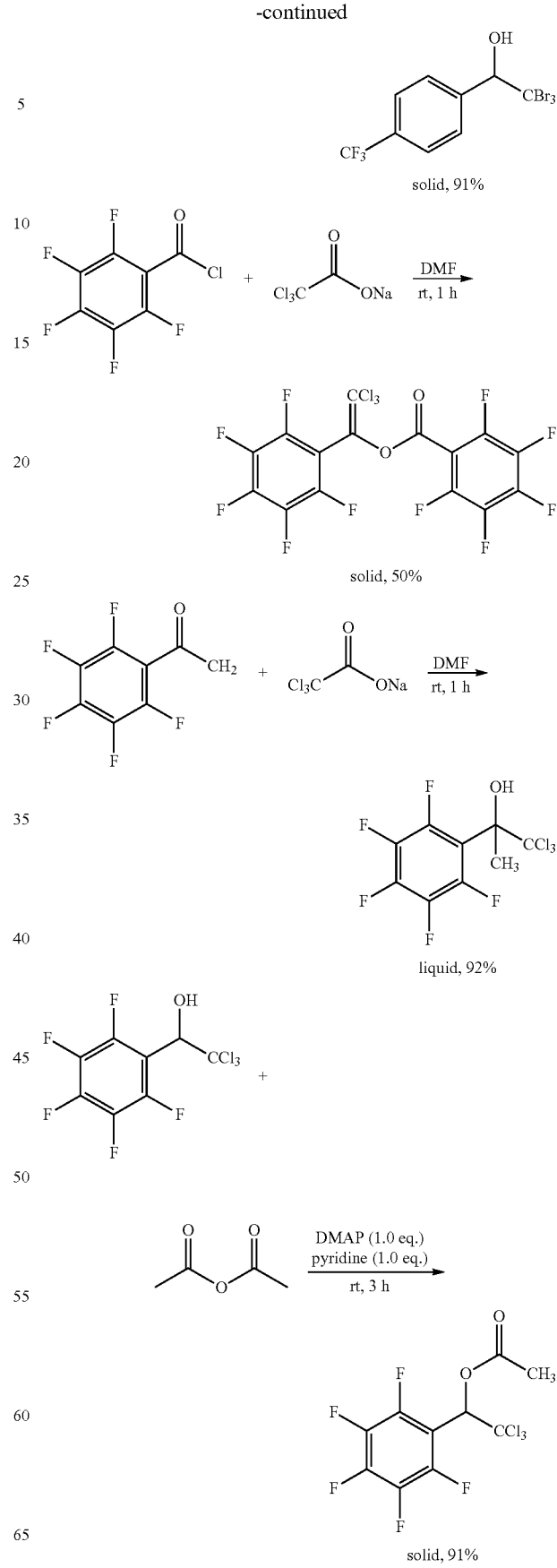

-continued

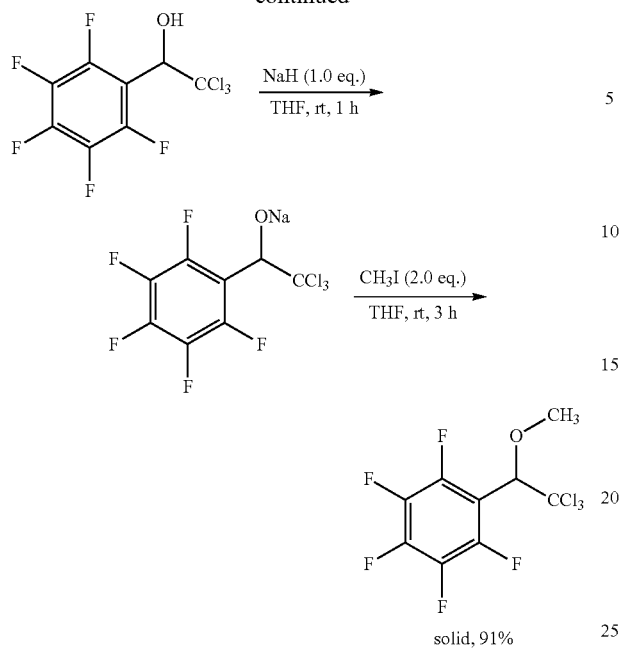

solid, 91%

Benzaldehyde (15.0 mmol) was dissolved in 20 mL of DMF, after cooling to 0° C., trichloroacetic acid (3.68 g, 22.5 mmol) was added to the solution. This was followed by the addition of sodium trichloroacetate (4.17 g, 22.5 mmol). Then the reaction mixture was stirred at room temperature and monitored by TLC (thin layer chromatography) (hexane/ethyl acetate: 1/4), during which there was an evolution of gas bubbles and complete dissolution of sodium trichloroacetate. After the reaction was completed, 50 mL of water was added to the solution. The mixture was extracted with ethyl acetate (3×40 mL). Organic extracts were combined and washed with saturated sodium bicarbonate solution (2×50 mL) (1, 2). The organic phase was dried with sodium sulfate and concentrated under reduced pressure. The resulting residue was purified by silica column chromatography (hexane/ethyl acetate: 1/19) to afford products.

Characterization of Exemplary Compounds According to the Present Disclosure:

Nuclear magnetic resonance (NMR). $^1$H NMR, $^{13}$C NMR and $^{19}$F NMR spectra were recorded on a Bruker AVIII 400 MHz spectrometer at 400 MHz, 100 MHz and 377 MHz, respectively. Chemical shifts are reported in parts per million (ppm) relative to the residual deuterated chloroform peak (7.26 ppm for $^1$H NMR and 77.23 for proton decoupled $^{13}$C NMR). $^{19}$F NMR chemical shifts of resulting reaction mixtures are reported with the external standard α,α,α-trifluorotoluene, δ −63.72. Data are represented as follows: chemical shift, multiplicity (br=broad, s=singlet, d=doublet, t=triplet, q=quartet, quint=quintet, sext=sextet, sept=septet, m=multiplet), coupling constants (J) in Hertz (Hz), integration.

High Performance Liquid Chromatography (HPLC). HPLC traces were obtained using an Agilent 1260 Infinity with CHIRALPAK OJ-H and OD-H columns. The column type, eluent (a mixture of n-hexane and iso-propanol), detector and enantiomeric excess (ee) are indicated for each experiment.

Example 5-1:
1-(4-fluorophenyl)-2,2,2-trichloro-ethanol

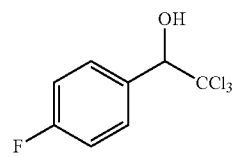

Colorless oil in 90% yield (3.27 g, 13.5 mmol).
$^1$H NMR (400 MHz, CDCl$_3$): δ=7.62-7.58 (m, 2H), 7.11-7.06 (m, 2H), 5.20 (s, 1H), 3.49 (s, 1H);
$^{13}$C NMR (100 MHz, CDCl$_3$): δ=163.59 (d, J=248.7 Hz), 131.24 (d, J=8.4 Hz), 130.78 (d, J=3.3 Hz), 115.04 (d, J=21.7 Hz), 103.22 (d, J=2.1 Hz), 84.01;
$^{19}$F NMR (377 MHz, CDCl$_3$): δ=−112.72 (s, 1F).

Example 5-2:
1-(3,4-difluorophenyl)-2,2,2-trichloro-ethanol

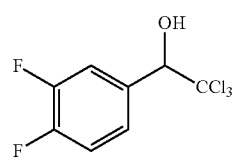

Colorless oil in 95% yield (3.74 g, 14.3 mmol).
$^1$H NMR (400 MHz, CDCl$_3$): δ=7.50 (ddd, J=11.3, 7.6, 2.2 Hz, 1H), 7.35 (ddt, J=8.1, 3.9, 1.8 Hz, 1H), 7.18 (dt, J=10.0, 8.3 Hz, 1H), 5.19 (s, 1H), 3.44-3.19 (m, 1H);
$^{13}$C NMR (100 MHz, CDCl$_3$): δ=151.24 (dd, J=250.0, 13.0 Hz), 149.99 (dd, J=246.0, 12.0 Hz),
131.17 (dd, J=5.7, 3.9 Hz), 125.94 (dd, J=6.7, 3.8 Hz), 118.58 (d, J=18.7 Hz), 116.79 (d, J=17.6 Hz), 102.82, 83.54 (d, J=1.6 Hz);
$^{19}$F NMR (377 MHz, CDCl$_3$): δ=−137.14 (d, J=21.1 Hz, 1F), −138.30 (d, J=21.2 Hz, 1F).

Example 5-3:
1-(2,4-difluorophenyl)-2,2,2-trichloro-ethanol

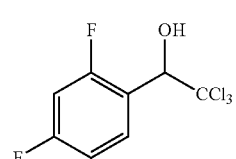

White solid in 92% yield (3.61 g, 13.8 mmol).
$^1$H NMR (400 MHz, CDCl$_3$): δ=7.79 (td, J=8.4, 6.4 Hz, 1H), 6.97 (tdd, J=7.9, 2.6, 1.1 Hz, 1H), 6.91-6.82 (m, 1H), 5.57 (s, 1H), 3.31 (d, J=2.0 Hz);
$^{13}$C NMR (100 MHz, CDCl$_3$): δ=163.77 (dd, J=250.0, 13.0 Hz), 161.03 (dd, J=250.0, 12.0 Hz), 131.10 (dd, J=10.0, 4.2 Hz), 119.10 (dd, J=12.1, 4.0 Hz), 111.60 (dd, J=21.5, 3.6 Hz), 103.80 (dd, J=26.4, 25.5 Hz), 102.72 (t, J=2.2 Hz), 77.20 (d, J=1.8 Hz);
$^{19}$F NMR (377 MHz, CDCl$_3$): δ=−108.64 (d, J=8.9 Hz, 1F), −110.50 (d, J=8.9 Hz, 1F).

Example 5-4:
1-(2,6-difluorophenyl)-2,2,2-trichloro-ethanol

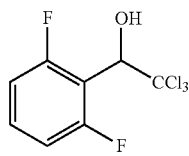

White solid in 90% yield (3.53 g, 13.5 mmol).
$^1$H NMR (400 MHz, CDCl$_3$): δ=7.39 (tt, J=8.5, 6.3 Hz, 1H), 7.04-6.90 (m, 2H), 5.58 (d, J=11.4 Hz, 1H), 3.92 (dt, J=11.5, 5.0 Hz, 1H);
$^{13}$C NMR (100 MHz, CDCl$_3$): δ=161.38 (dd, J=251.4, 6.2 Hz), 131.79 (t, J=11.2 Hz), 112.44, 112.43 (d, J=24.0 Hz), 102.12 (d, J=2.1 Hz), 79.52;
$^{19}$F NMR (377 MHz, CDCl$_3$): δ=−109.41 (s, 2F).

Example 5-5:
1-(3,4,5-trifluorophenyl)-2,2,2-trichloro-ethanol

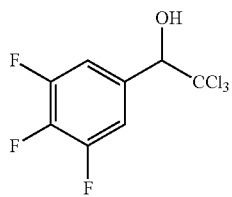

Colorless oil in 95% yield (4.00 g, 14.3 mmol).
$^1$H NMR (400 MHz, CDCl$_3$): δ=7.50-7.06 (m, 2H), 5.15 (d, J=3.5 Hz, 1H), 3.48 (d, J=3.6 Hz, 1H);
$^{13}$C NMR (100 MHz, CDCl$_3$): δ=150.77 (ddd, J=250.1, 10.1, 3.8 Hz), 140.61 (dt, J=254.3, 15.2 Hz), 130.88 (td, J=7.6, 4.7 Hz), 115.10=112.15 (m), 102.36, 83.13 (d, J=2.1 Hz);
$^{19}$F NMR (377 MHz, CDCl$_3$): δ=−134.05 (d, J=20.5 Hz, 2F), −158.51 (t, J=20.5 Hz, 1F).

Example 5-6:
1-(2,4,6-trifluorophenyl)-2,2,2-trichloro-ethanol

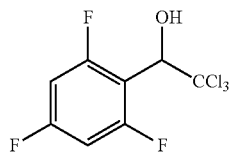

White solid in 97% yield (4.08 g, 14.6 mmol).
$^1$H NMR (400 MHz, CDCl$_3$): δ=6.80-6.69 (m, 2H), 5.52 (d, J=10.8 Hz, 1H), 3.81 (dt, J=11.0, 3.9 Hz, 1H);
$^{13}$C NMR (100 MHz, CDCl$_3$): δ=163.57 (dt, J=253.5, 16.6 Hz), 161.80 (dt, J=255.3, 12.2 Hz), 108.99 (td, J=14.9, 5.1 Hz), 101.99 (d, J=2.0 Hz), 101.41 (t, J=27.2 Hz), 79.27 (J=Hz);
$^{19}$F NMR (377 MHz, CDCl$_3$): δ=−104.91 (t, J=8.2 Hz, 1F), −105.07 (s, 2F).

Example 5-7:
1-(2,4,5-trifluorophenyl)-2,2,2-trichloro-ethanol

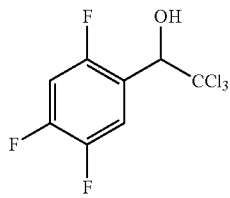

White solid in 93% yield (3.91 g, 14.0 mmol).
$^1$H NMR (400 MHz, CDCl$_3$): δ=7.62 (ddd, J=10.8, 8.8, 6.3 Hz, 1H), 6.96 (td, J=9.6, 6.4 Hz, 1H), 5.55 (s, 1H), 3.42 (s, 1H);
$^{13}$C NMR (100 MHz, CDCl$_3$): δ=156.05 (ddd, J=248.3, 9.7, 2.7 Hz), 151.12 (ddd, J=254.4, 14.5, 12.7 Hz), 146.93 (ddd, J=245.5, 12.6, 3.5 Hz), 119.33 (ddd, J=14.3, 5.5, 4.3 Hz), 118.11 (ddd, J=20.8, 4.2, 1.6 Hz), 105.51 (dd, J=28.7, 21.0 Hz), 102.32, 76.85;
$^{19}$F NMR (377 MHz, CDCl$_3$): δ=−115.74 (dd, J=15.1, 5.3 Hz, 1F), −131.79 (dd, J=21.5, 5.3 Hz, 1F), −142.46 (dd, J=21.7, 15.0 Hz, 1F).

Example 5-8:
1-perfluorophenyl-2,2,2-trichloro-ethanol

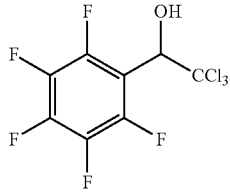

White solid in 96% yield (4.54 g, 14.4 mmol).
$^1$H NMR (400 MHz, CDCl$_3$): δ=5.58 (d, J=7.8 Hz, 1H), 3.72 (dt, J=9.8, 4.0 Hz, 1H);
$^{13}$C NMR (100 MHz, CDCl$_3$, only nonaromatic carbons reported): δ=101.08, 79.41 (q, J=1.7 Hz);
$^{19}$F NMR (377 MHz, CDCl$_3$): δ=−137.06 (s, 2F), −151.61 (tt, J=21.0, 3.8 Hz, 1F), −161.69 (s, 2F).

Example 5-9: 1-(4-(trifluoromethyl)phenyl)-2,2,2-trichloro-ethanol

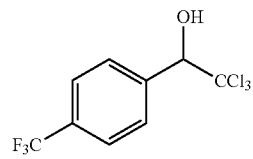

White solid in 95% yield (4.20 g, 14.3 mmol).
$^1$H NMR (400 MHz, CDCl$_3$): δ=7.76 (d, J=8.2 Hz, 2H), 7.66 (d, J=8.2 Hz, 2H), 5.27 (d, J=2.9 Hz, 1H), 3.54 (d, J=3.8 Hz, 1H);

$^{13}$C NMR (100 MHz, CDCl$_3$): δ=138.70 (d, J=1.5 Hz), 131.74 (q, J=32.6 Hz), 129.93, 124.93 (q, J=3.8 Hz), 124.10 (q, J=272.3 Hz), 102.64, 84.03;

$^{19}$F NMR (377 MHz, CDCl$_3$): δ=−63.72 (s, 3F).

Example 5-10: 1-(4-(trifluoromethoxy)phenyl)-2,2,2-trichloro-ethanol

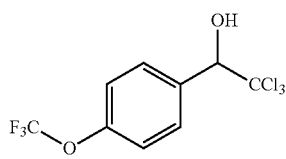

Colorless oil in 97% yield (4.52 g, 14.6 mmol).

$^1$H NMR (400 MHz, CDCl$_3$): δ=7.68-7.65 (m, 2H), 7.25-7.22 (m, 2H), 5.23 (s, 1H), 3.42 (s, 1H);

$^{13}$C NMR (100 MHz, CDCl$_3$): δ=150.19 (q, J=2.0 Hz), 133.43, 131.03, 120.61 (q, J=256.0 Hz), 120.27, 102.98, 83.93;

$^{19}$F NMR (377 MHz, CDCl$_3$): δ=−58.73 (s, 3F).

Example 5-11: 1-(4-(trifluoromethyl)thio)phenyl)-2,2,2-trichloro-ethanol

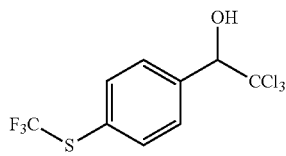

White solid in 88% yield (4.30 g, 13.2 mmol).

$^1$H NMR (400 MHz, CDCl$_3$): δ=7.69 (s, 4H), 5.26 (d, J=3.7 Hz, 1H), 3.36 (d, J=3.8 Hz, 1H);

$^{13}$C NMR (100 MHz, CDCl$_3$): δ=137.68, 135.62, 130.55, 129.67 (q, J=306.0 Hz), 126.09 (q, J=2.1 Hz), 102.70, 84.06;

$^{19}$F NMR (377 MHz, CDCl$_3$): δ=−43.28 (s, 3F).

Example 5-12: 1-(4-methoxyphenyl)-2,2,2-trichloro-ethanol

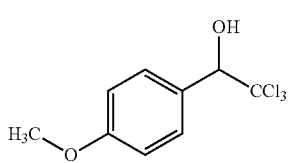

White solid in 81% yield (3.12 g, 12.2 mmol).

$^1$H NMR (400 MHz, CDCl$_3$): δ=7.60-7.49 (m, 2H), 6.96-6.87 (m, 2H), 5.17 (s, 1H), 3.83 (s, 3H), 3.28 (s, 1H);

$^{13}$C NMR (100 MHz, CDCl$_3$): δ=160.62, 130.60, 127.10, 113.45, 103.72, 84.40, 55.49.

Example 5-13: 1-(6-(trifluoromethyl)pyridin-3-yl)-2,2,2-trichloro-ethanol

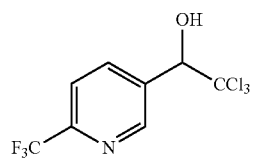

White solid in 97% yield (4.30 g, 14.6 mmol).

$^1$H NMR (400 MHz, CDCl$_3$): δ=8.94 (d, J=2.1 Hz, 1H), 8.20 (dd, J=8.2, 2.1 Hz, 1H), 7.74 (dd, J=8.2, 0.8 Hz, 1H), 5.36 (d, J=3.2 Hz, 1H), 3.69 (d, J=3.7 Hz, 1H);

$^{13}$C NMR (100 MHz, CDCl$_3$): δ=150.88, 149.03 (d, J=34.9 Hz), 138.55, 133.99, 121.53 (q, J=274.4 Hz), 119.94 (q, J=2.7 Hz), 102.14, 82.22;

$^{19}$F NMR (377 MHz, CDCl$_3$): δ=−68.89 (s, 3F).

Example 5-14: 1-(4-nitrophenyl)-2,2,2-trichloro-ethanol

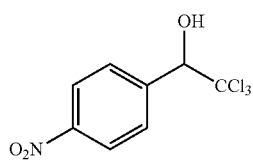

Yellow solid in 85% yield (3.46 g, 12.8 mmol).

$^1$H NMR (400 MHz, CDCl$_3$): δ=8.29-8.20 (m, 2H), 7.89-7.79 (m, 2H), 5.34 (s, 1H), 3.57 (s, 1H);

$^{13}$C NMR (100 MHz, CDCl$_3$): δ=148.72, 141.58, 130.60, 123.05, 102.55, 83.65.

Example 5-15: 1-(4-cyanophenyl)-2,2,2-trichloro-ethanol

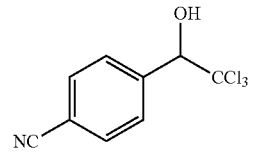

White solid in 85% yield (3.21 g, 12.8 mmol).

$^1$H NMR (400 MHz, CDCl$_3$): δ=7.80-7.73 (m, 2H), 7.72-7.65 (m, 2H), 5.27 (d, J=3.0 Hz, 1H), 3.64 (d, J=3.7 Hz, 1H);

$^{13}$C NMR (100 MHz, CDCl$_3$): δ=139.96, 131.69, 130.31, 118.56, 113.40, 102.33, 83.78.

Example 5-16: 1-(2-fluoro-4-(trifluoromethyl)phenyl)-2,2,2-trichloro-ethanol

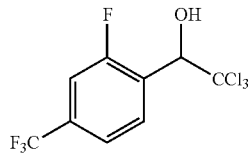

White solid in 90% yield (4.20 g, 13.5 mmol).
$^1$H NMR (400 MHz, CDCl$_3$): δ=7.94 (t, J=7.4 Hz, 1H), 7.50 (dd, J=8.2, 1.6 Hz, 1H), 7.37 (dd, J=9.9, 1.7 Hz, 1H), 5.66 (d, J=4.6 Hz, 1H), 3.40 (d, J=4.6 Hz, 1H);
$^{13}$C NMR (100 MHz, CDCl$_3$): δ=160.43 (d, J=251.6 Hz), 133.67 (qd, J=33.6, 8.5 Hz), 131.05 (d, J=2.9 Hz), 126.81 (d, J=11.1 Hz), 123.22 (qd, J=272.7, 2.8 Hz), 121.02 (p, J=3.8 Hz), 113.09 (dq, J=26.0, 3.9 Hz), 102.18, 77.20 (d, J=1.8 Hz);
$^{19}$F NMR (377 MHz, CDCl$_3$): δ=−64.01 (s, 3F), −111.84 (s, 1F).

Example 5-17: 1-(2,4-bis(trifluoromethyl)phenyl)-2,2,2-trichloro-ethanol

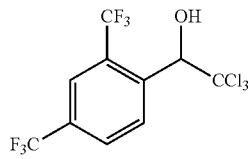

Colorless oil in 95% yield (5.17 g, 14.3 mmol).
$^1$H NMR (400 MHz, CDCl$_3$): δ=8.36 (d, J=8.4 Hz, 1H), 7.98 (d, J=1.8 Hz, 1H), 7.90 (dd, J=8.4, 1.8 Hz, 1H), 5.81 (d, J=4.3 Hz, 1H), 3.46 (d, J=4.6 Hz, 1H);
$^{13}$C NMR (100 MHz, CDCl$_3$): δ=138.34, 132.28 (q, J=33.8 Hz), 130.78 (q, J=30.7 Hz), 130.44, 128.80 (d, J=3.9 Hz), 123.60 (td, J=8.5, 7.7, 4.9 Hz), 123.45 (q, J=274.8 Hz), 123.26 (q, J=272.6 Hz), 101.73, 78.95 (q, J=3.0 Hz);
$^{19}$F NMR (377 MHz, CDCl$_3$): δ=−57.21 (s, 3F), −64.71 (s, 3F).

Example 5-18: 1-(2-fluoro-4-(trifluoromethoxy)phenyl)-2,2,2-trichloro-ethanol

Colorless oil in 90% yield (4.42 g, 13.5 mmol).
$^1$H NMR (400 MHz, CDCl$_3$): δ=7.83 (t, J=8.2 Hz, 1H), 7.09 (dq, J=7.7, 1.2 Hz, 1H), 6.99 (ddd, J=10.4, 2.3, 1.1 Hz, 1H), 5.60 (d, J=4.2 Hz, 1H), 3.54 (d, J=4.4 Hz, 1H);
$^{13}$C NMR (100 MHz, CDCl$_3$): δ=160.81 (d, J=251.9 Hz), 150.79 (dq, J=11.4, 1.7 Hz), 133.55-128.84 (m), 121.60 (d, J=12.1 Hz), 120.49 (q, J=258.9 Hz), 116.34 (d, J=3.6 Hz), 108.53 (dd, J=26.8, 1.5 Hz), 102.47 (d, J=2.5 Hz), 77.19 (d, J=1.7 Hz);
$^{19}$F NMR (377 MHz, CDCl$_3$): δ=−58.98 (s, 3F), −110.56 (s, 1F).

Example 5-19: 1-(2,6-dichloro-4-(trifluoromethyl)phenyl)-2,2,2-trichloro-ethanol

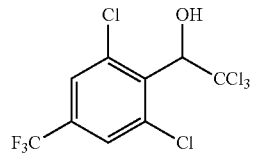

White solid in 80% yield (4.35 g, 12.0 mmol).
$^1$H NMR (400 MHz, CDCl$_3$): δ=7.68 (d, J=1.8 Hz, 1H), 7.62 (d, J=1.8 Hz, 1H), 6.20 (d, J=11.7 Hz, 1H), 4.53 (d, J=11.7 Hz, 1H);
$^{13}$C NMR (100 MHz, CDCl$_3$): δ=139.44, 135.05, 134.40, 133.12, (q, J=34.5 Hz), 128.12 (q, J=3.7 Hz), 126.31 (q, J=3.7 Hz), 122.30 (q, J=272 Hz), 101.64, 83.44;
$^{19}$F NMR (377 MHz, CDCl$_3$): δ=−64.37 (s, 3F).

Example 5-20: 1-(4-fluoro-3-phenoxyphenyl)-2,2,2-trichloro-ethanol

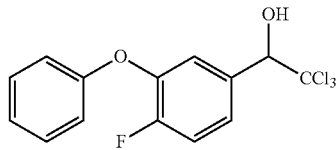

White solid in 85% yield (4.30 g, 12.8 mmol).
$^1$H NMR (400 MHz, CDCl$_3$): δ=7.45-7.29 (m, 4H), 7.20 (dd, J=10.2, 8.4 Hz, 1H), 7.15-7.06 (m, 1H), 7.04-6.94 (m, 2H), 5.15 (d, J=2.8 Hz, 1H), 3.38 (d, J=3.4 Hz, 1H);
$^{13}$C NMR (100 MHz, CDCl$_3$): δ=157.32, 155.03 (d, J=251.7 Hz), 143.33 (d, J=11.8 Hz), 131.63 (d, J=3.7 Hz), 129.98, 125.82 (d, J=7.3 Hz), 123.58, 123.07 (d, J=1.8 Hz), 117.52, 116.60 (d, J=18.9 Hz), 103.07 (d, J=2.2 Hz), 83.77;
$^{19}$F NMR (377 MHz, CDCl$_3$): δ=−130.32 (s, 1F).

Example 5-21: 1-(4-fluoro-3-methylphenyl)-2,2,2-trichloro-ethanol

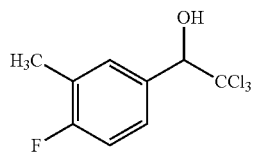

White solid in 80% yield (3.09 g, 12.0 mmol).
$^1$H NMR (400 MHz, CDCl$_3$): δ=7.45 (d, J=7.4 Hz, 1H), 7.41 (dd, J=9.0, 4.7 Hz, 1H), 7.02 (t, J=8.9 Hz, 1H), 5.17 (s, 1H), 3.29 (s, 1H), 2.31 (s, 3H);

$^{13}$C NMR (100 MHz, CDCl$_3$): δ=162.12 (d, J=247.5 Hz), 132.48 (d, J=5.6 Hz), 130.39 (d, J=3.7 Hz), 128.58 (d, J=8.4 Hz), 124.67 (d, J=17.6 Hz), 114.66 (d, J=22.8 Hz), 103.33 (d, J=2.0 Hz), 84.17, 14.87 (d, J=3.6 Hz);
$^{19}$F NMR (377 MHz, CDCl$_3$): δ=116.98 (s, 1F).

Example 5-22: 1-(3-(trifluoromethyl)phenyl)-2,2,2-trichloro-ethanol

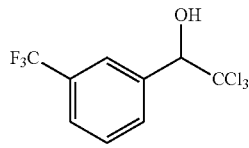

Colorless liquid in 91% yield (4.02 g, 13.7 mmol).
$^1$H NMR (400 MHz, CDCl$_3$): δ=7.91 (s, 1H), 7.82 (d, J=7.9 Hz, 1H), 7.68 (d, J=7.9 Hz, 1H), 7.52 (t, J=7.8 Hz, 1H), 5.28 (d, J=3.6 Hz, 1H), 3.42 (d, J=3.7 Hz, 1H);
$^{13}$C NMR (100 MHz, CDCl$_3$): δ=135.82, 132.86 (d, J=1.4 Hz), 130.54 (q, J=32.6 Hz), 128.48, 126.49 (q, J=3.8 Hz), 126.38 (q, J=4.0 Hz), 124.13 (q, J=272.3 Hz), 102.72, 84.05;
$^{19}$F NMR (377 MHz, CDCl$_3$): δ=−63.61 (s, 3F).

Example 5-23: 1-(4-fluoro-2-(trifluoromethyl)phenyl)-2,2,2-trichloro-ethanol

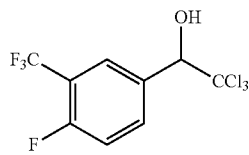

Colorless liquid in 92% yield (4.30 g, 13.8 mmol).
$^1$H NMR (400 MHz, CDCl$_3$): δ=7.90 (dd, J=6.9, 1.9 Hz, 1H), 7.83 (ddd, J=7.6, 4.4, 2.2 Hz, 1H), 7.22 (t, J=9.3 Hz, 1H), 5.26 (d, J=3.5 Hz, 1H), 3.43 (d, J=3.6 Hz, 1H);
$^{13}$C NMR (100 MHz, CDCl$_3$): δ=160.48 (dq, J=259.0, 2.0 Hz), 135.07 (d, J=8.9 Hz), 131.12 (d, J=3.9 Hz), 128.44 (qd, J=4.7, 2.0 Hz), 122.58 (qd, J=272.5, 1.0 Hz), 118.23 (qd, J=33.3, 12.8 Hz), 116.63 (d, J=21.0 Hz), 102.67 (d, J=1.9 Hz), 83.45;
$^{19}$F NMR (377 MHz, CDCl$_3$): δ=−62.41 (d, J=12.5 Hz, 3F), −114.00 (q, J=12.7 Hz, 1F).

Example 5-24: 1-(4-phenoxyphenyl)-2,2,2-trichloro-ethanol

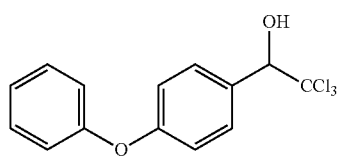

White solid in 80% yield (3.81 g, 12.0 mmol).
$^1$H NMR (400 MHz, CDCl$_3$): δ=7.59-7.54 (m, 2H), 7.40-7.33 (m, 2H), 7.18-7.12 (m, 1H), 7.08-7.03 (m, 2H), 7.02-6.97 (m, 2H), 5.21 (d, J=3.7 Hz, 1H), 3.29 (d, J=3.9 Hz, 1H);

$^{13}$C NMR (100 MHz, CDCl$_3$): δ=158.76, 156.61, 130.87, 130.08, 129.35, 124.07, 119.77, 117.71, 103.50, 84.32.

Example 5-25: 1-(4'-fluoro-[1,1'-biphenyl]-4-yl)-2,2,2-trichloro-ethanol

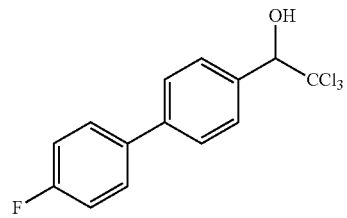

White solid in 85% yield (4.09 g, 12.8 mmol).
$^1$H NMR (400 MHz, CDCl$_3$): δ=7.71-7.67 (m, 2H), 7.56 (ddd, J=8.8, 3.8, 2.1 Hz, 4H), 7.17-7.10 (m, 2H), 5.27 (d, J=3.8 Hz, 1H), 3.34 (d, J=4.0 Hz, 1H);
$^{13}$C NMR (100 MHz, CDCl$_3$): δ=162.87 (d, J=246.9 Hz), 141.55, 136.73 (d, J=3.3 Hz), 133.95, 129.90, 128.97 (d, J=8.1 Hz), 126.60, 115.95 (d, J=21.4 Hz), 103.32, 84.51;
$^{19}$F NMR (377 MHz, CDCl$_3$): δ=116.09 (s, 1F).

Example 5-26: 1-(3-bromo-4-fluorophenyl)-2,2,2-trichloro-ethanol

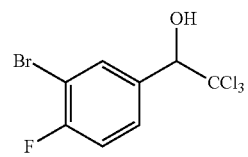

White solid in 90% yield (4.35 g, 13.5 mmol).
$^1$H NMR (400 MHz, CDCl$_3$): δ=7.84 (dd, J=6.5, 2.2 Hz, 1H), 7.55 (ddd, J=8.6, 4.6, 2.2 Hz, 1H), 7.14 (t, J=8.4 Hz, 1H), 5.18 (d, J=3.4 Hz, 1H), 3.42 (d, J=3.6 Hz, 1H);
$^{13}$C NMR (100 MHz, CDCl$_3$): δ=159.85 (d, J=250.1 Hz), 134.56, 132.22 (d, J=3.9 Hz), 130.26 (d, J=7.7 Hz), 115.99 (d, J=22.7 Hz), 108.78 (d, J=21.3 Hz), 102.82 (d, J=2.0 Hz), 83.37;
$^{19}$F NMR (377 MHz, CDCl$_3$): δ=−106.76 (s, 1F).

Example 5-27: 1-(2-fluoro-5-(trifluoromethyl)phenyl)-2,2,2-trichloro-ethanol

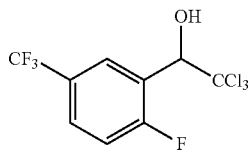

Colorless liquid in 90% yield (4.20 g, 13.5 mmol).
$^1$H NMR (400 MHz, CDCl$_3$): δ=8.09 (dd, J=6.3, 2.3 Hz, 1H), 7.68 (ddd, J=8.6, 4.7, 2.4 Hz, 1H), 7.21 (t, J=9.1 Hz, 1H), 5.66 (d, J=4.2 Hz, 1H), 3.53 (d, J=4.4 Hz, 1H);
$^{13}$C NMR (100 MHz, CDCl$_3$): δ=162.46 (dd, J=254.9, 1.6 Hz), 128.72 (dq, J=10.3, 3.6 Hz), 127.93 (p, J=3.9 Hz), 126.98 (qd, J=33.3, 3.4 Hz), 123.94 (d, J=13.2 Hz), 123.77 (q, J=272.1 Hz), 116.26 (d, J=24.0 Hz), 102.22 (d, J=2.3 Hz), 77.04 (d, J=1.8 Hz);

$^{19}$F NMR (377 MHz, CDCl$_3$): δ=−63.08 (d, J=1.6 Hz, 3F), −108.86 (d, J=1.7 Hz, 1F).

Example 5-28: 1-(3-bromo-5-(trifluoromethyl)phenyl)-2,2,2-trichloro-ethanol

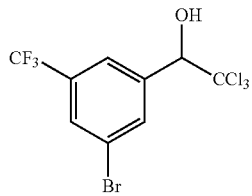

White solid in 85% yield (4.77 g, 12.8 mmol).

$^1$H NMR (400 MHz, CDCl$_3$): δ=7.98 (d, J=1.8 Hz, 1H), 7.85-7.78 (m, 2H), 5.24 (s, 1H), 3.50 (s, 1H);

$^{13}$C NMR (100 MHz, CDCl$_3$): δ=137.85, 135.84, 132.07 (q, J=33.3 Hz), 129.68 (q, J=3.8 Hz), 125.23 (q, J=3.8 Hz), 123.15 (q, J=273.0 Hz), 122.31, 102.22, 83.35;

$^{19}$F NMR (377 MHz, CDCl$_3$): δ=−63.75 (s, 3F).

Example 5-29: Synthesis of 1-(4-(trifluoromethyl)phenyl)-2,2,2-tribromo-ethanol

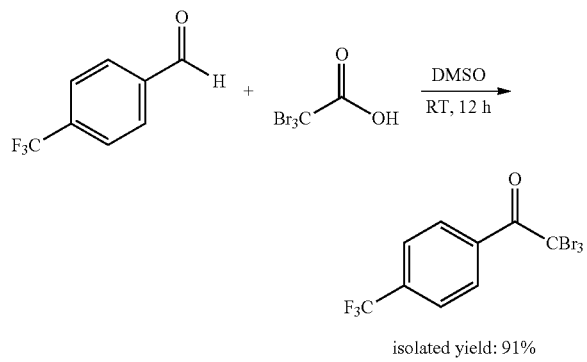

isolated yield: 91%

4-(trifluoromethyl)benzaldehyde (2.61 g, 15 mmol) was dissolved in 20 mL of DMSO, after cooling to 0° C., tribromoacetic acid (6.05 g, 22.5 mmol) was added to the solution. Then the reaction mixture was stirred overnight at room temperature. After the reaction was completed, 50 mL of water was added to the solution. The mixture was extracted with ethyl acetate (3×50 mL). Organic extracts were combined and washed with saturated sodium chloride solution (2×50 mL). (3) The organic phase was dried with sodium sulfate and concentrated under reduced pressure. The resulting residue was purified by silica column chromatography (hexane/ethyl acetate: 1/19) to afford the product (5.83 g, 13.7 mmol).

Example 5-29: 1-(4-(trifluoromethyl)phenyl)-2,2,2-tribromo-ethanol

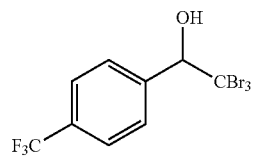

White solid in 91% yield (5.85 g, 13.7 mmol).

$^1$H NMR (400 MHz, CDCl$_3$): δ=7.86 (d, J=8.1 Hz, 2H), 7.65 (d, J=8.2 Hz, 2H), 5.25 (d, J=3.4 Hz, 1H), 3.62 (d, J=3.7 Hz, 1H);

$^{13}$C NMR (100 MHz, CDCl$_3$): δ=139.02 (d, J=1.4 Hz), 131.62 (q, J=32.6 Hz), 130.36, 124.75 (q, J=3.8 Hz), 124.13 (q, J=272.3 Hz), 85.25, 53.29;

$^{19}$F NMR (377 MHz, CDCl$_3$): δ=−63.72 (s, 3F).

Example 5-30: Synthesis of 2-(perfluorophenyl)-1,1,1-trichloro-propan-2-ol

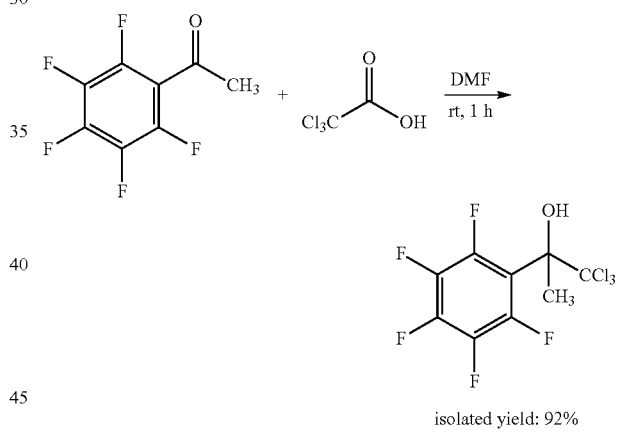

isolated yield: 92%

1-(perfluorophenyl)-ethan-1-one (3.15 g, 15 mmol) was dissolved in 20 mL of DMF, after cooling to 0° C., trichloroacetic acid (3.68 g, 22.5 mmol) was added to the solution. This was followed by the addition of sodium trichloroacetate (4.17 g, 22.5 mmol). Then the reaction mixture was stirred at room temperature and monitored by TLC (thin layer chromatography) (hexane/ethyl acetate: 1/4), during which there was an evolution of gas bubbles and complete dissolution of sodium trichloroacetate. After the reaction was completed, 50 mL of water was added to the solution. The mixture was extracted with ethyl acetate (3×40 mL). Organic extracts were combined and washed with saturated sodium bicarbonate solution (2×50 mL) (1, 2). The organic phase was dried with sodium sulfate and concentrated under reduced pressure. The resulting residue was purified by silica column chromatography (hexane/ethyl acetate: 1/19) to afford the product (4.54 g, 13.8 mmol).

Example 5-30:
2-(perfluorophenyl)-1,1,1-trichloro-propan-2-ol

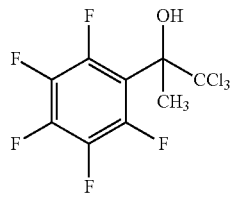

Colorless oil in 92% yield (4.55 g, 13.8 mmol).
$^1$H NMR (400 MHz, CDCl$_3$): δ=4.39-4.23 (m, 1H), 2.12 (t, J=3.3 Hz, 3H);
$^{13}$C NMR (100 MHz, CDCl$_3$, only nonaromatic carbons reported): δ=106.74, 86.64, 25.76 (t, J=6.6 Hz);
$^{19}$F NMR (377 MHz, CDCl$_3$): δ=−128.93 (s, 1F), −137.24 (s, 1F), −151.47 (tt, J=21.4, 5.1 Hz, 1F), −160.76 (s, 2F).

Example 5-31: Synthesis of 1-(perfluorophenyl)-2,2,2-trichloro-ethyl acetate

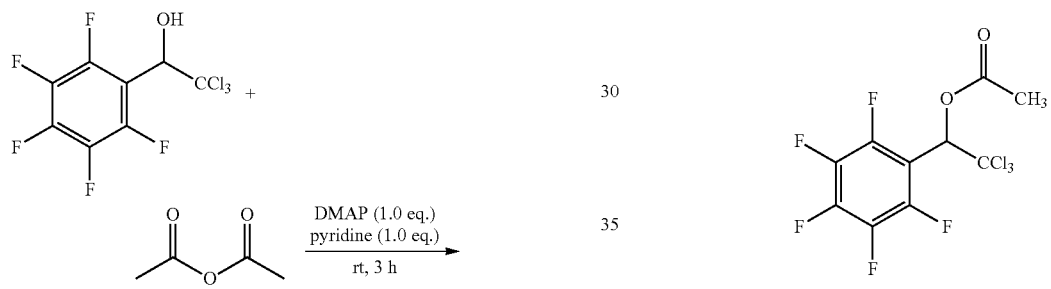

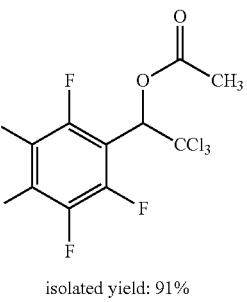

isolated yield: 91%

To a solution of 1-(perfluorophenyl)-2,2,2-trichloro-ethanol (0.50 g, 1.6 mmol) and DMAP (0.20 g, 1.6 mmol) in pyridine (0.16 g, 2.0 mmol) at 0° C. was added acetic anhydride (0.49 g, 4.8 mmol). The reaction mixture was stirred at room temperature for three hours. The mixture was then quenched by 50 mL of water and extracted with ethyl acetate (3×50 mL). Organic extracts were combined and washed with dilute hydrochloric acid (2×50 mL), saturated sodium bicarbonate solution (2×50 mL) and saturated sodium chloride solution (2×50 mL) (4). The organic phase was dried with sodium sulfate and concentrated under reduced pressure. The resulting residue was purified by silica column chromatography (hexane/ethyl acetate: 1/49) to afford the product (0.52 g, 1.46 mmol).

Example 5-31:
1-(perfluorophenyl)-2,2,2-trichloro-ethyl acetate

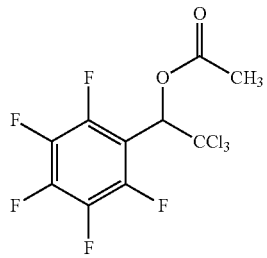

White solid in 91% yield (4.90 g, 13.7 mmol).
$^1$H NMR (400 MHz, CDCl$_3$): δ=6.64 (s, 1H), 2.25 (s, 3H);
$^{13}$C NMR (100 MHz, CDCl$_3$, only nonaromatic carbons reported): δ=168.84, 97.53, 76.56, 20.56;
$^{19}$F NMR (377 MHz, CDCl$_3$): δ=−135.49 (s, 2F), −150.86 (tt, J=21.1, 4.2 Hz, 1F), −161.68 (s, 2F).

General asymmetric synthesis of fluorinated 2,2,2-trichloro-1-phenylethan-1-ol

Scheme 5: asymmetric synthesis of fluorinated 2,2,2-trichloro-1-phenylethan-1-ol

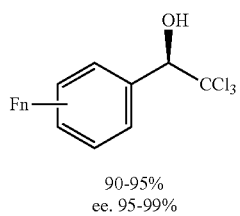

90-95%
ee. 95-99%

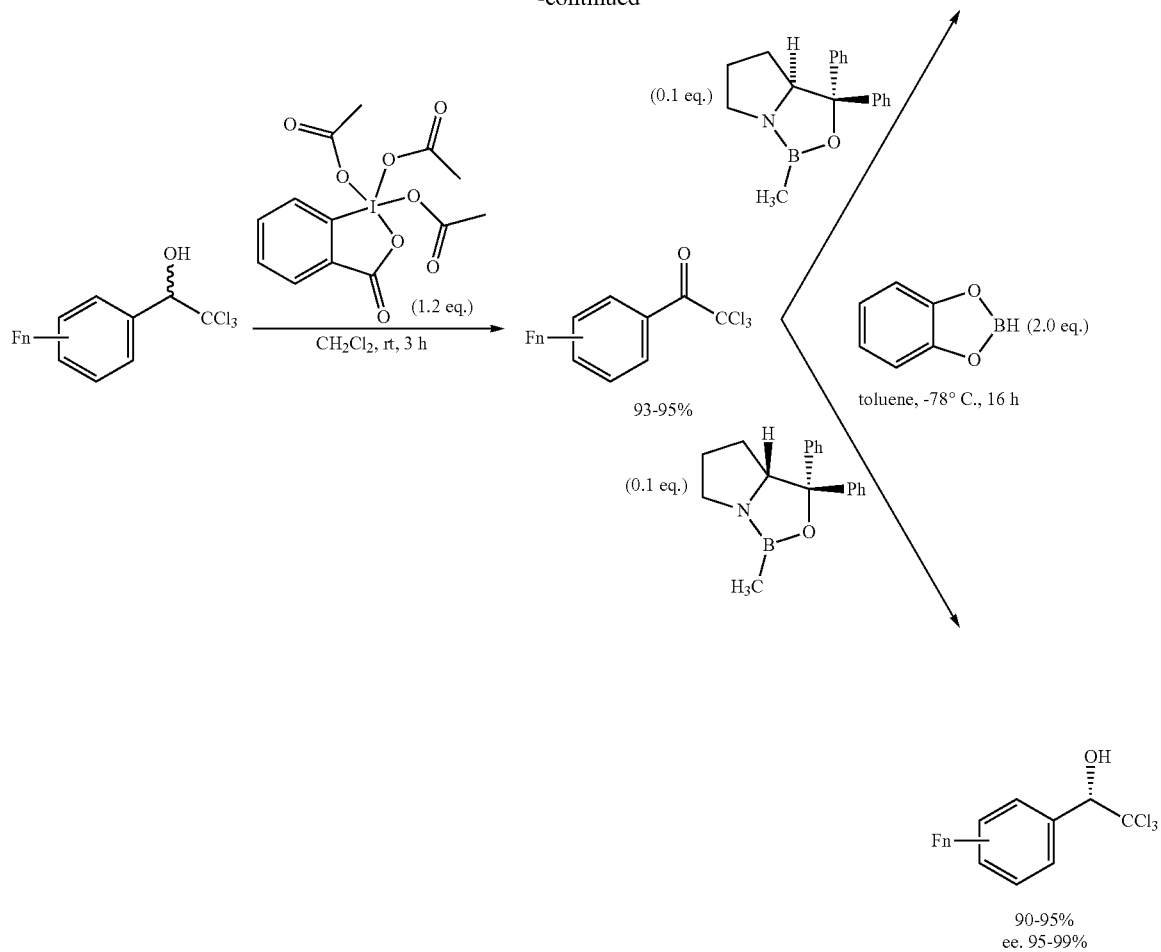

The racemic 1-phenyl-2,2,2-trichloro-ethanol (21.0 mmol) was added to a stirred suspension of Dess-Martin reagent (10.8 g, 22.5 mmol) in 100 mL CH$_2$Cl$_2$, and the reaction mixture was stirred at room temperature for 3 hours. The reaction was quenched with 50 mL saturated aqueous sodium bicarbonate and 50 mL sodium thiosulfate (20%) solution, and then stirred for 10 min. The aqueous layer was extracted with CH$_2$Cl$_2$ (50 mL×3). Organic extracts were combined and washed with saturated sodium chloride solution (2×50 mL) (5). The organic phase was dried with sodium sulfate and concentrated under reduced pressure. The resulting residue was purified by silica column chromatography (hexane/ethyl acetate: 1/09) to afford the product in 93-95% yields.

Under nitrogen, to a solution of fluorinated 1-phenyl-2,2,2-trichloro-ethanone (3.20 mmol) in toluene (25.0 mL) was added a 1M solution of oxazaborolidine catalyst in THF (0.32 mL) at room temperature ((R)-oxazaborolidine catalyst for the production of (S)-fluorinated 1-phenyl-2,2,2-trichloro-ethanol; ((S)-oxazaborolidine catalyst for the production of (R)-fluorinated 1-phenyl-2,2,2-trichloro-ethanol). The reaction mixture was cooled to −78° C. and 6.40 mL 1M solution of catechol borane in THF was added dropwise. The reaction was stirred at −78° C. for 6 hours and then at room temperature for 10 hours. The mixture was quenched by 150 mL of water and extracted with ethyl acetate (3×50 mL). Organic extracts were combined and washed with a 1M aqueous sodium hydroxide solution (3×75 mL), a 1 M aqueous hydrochloric acid solution (3×50 mL), and a saturated sodium chloride solution (2×50 mL). The organic phase was dried with sodium sulfate and concentrated under reduced pressure. The resulting residue was purified by silica column chromatography (hexane/ethyl acetate: 1/49) to afford the product in 90-95% yields. The enantiomeric excess was determined by HPLC analysis.

Example 5-32:
1-(4-fluorophenyl)-2,2,2-trichloro-ethanone

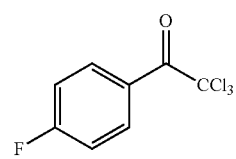

Colorless liquid in 93% yield (4.71 g, 19.5 mmol).
$^1$H NMR (400 MHz, CDCl$_3$): δ=8.36-8.26 (m, 2H), 7.21-7.13 (m, 2H);
$^{13}$C NMR (100 MHz, CDCl$_3$): δ=179.76, 166.19 (d, J=258.3 Hz), 134.50 (d, J=9.6 Hz), 125.22 (d, J=3.2 Hz), 115.78 (d, J=22.0 Hz), 95.25;
$^{19}$F NMR (377 MHz, CDCl$_3$): δ=−102.86 (s, 1F).

Example 5-33: 1-(perfluorophenyl)-2,2,2-trichloro-ethanone

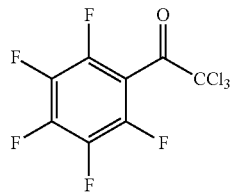

Colorless liquid in 95% yield (6.27 g, 20.0 mmol).

$^{13}$C NMR (100 MHz, CDCl$_3$, only nonaromatic carbons reported): δ=177.61, 94.40;

$^{19}$F NMR (377 MHz, CDCl$_3$): δ=−134.61-134.90 (m, 2F), −148.54 (tt, J=20.6, 3.9 Hz, 1F), −159.78-160.04 (m, 2F).

Example 5-34: (R)-1-(4-fluorophenyl)-2,2,2-trichloro-ethanol

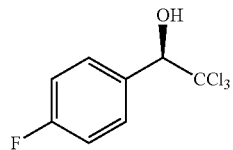

Colorless oil in 90% yield (0.70 g, 2.88 mmol), 95.28% ee.

All physical and spectroscopic data were identical to racemic 1-(4-fluorophenyl)-2,2,2-trichloro-ethanol. HPLC CHIRALPAK OD-H column (5% isopropanol in hexane, 0.7 mL/min), detection: UV 210, retention time: t$_r$=14.160 min (major), 17.715 min (minor), 95.28% ee.

Example 5-35: (S)-1-(4-fluorophenyl)-2,2,2-trichloro-ethanol

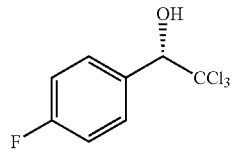

Colorless oil in 90% yield (0.70 g, 2.88 mmol), 94.38% ee.

All physical and spectroscopic data were identical to racemic 1-(4-fluorophenyl)-2,2,2-trichloro-ethanol. HPLC CHIRALPAK OD-H column (5% isopropanol in hexane, 0.7 mL/min), detection: UV 210, retention time: t$_r$=13.355 min (minor), 16.503 min (major), 94.38% ee.

Example 5-36: (R)-1-perfluorophenyl-2,2,2-trichloro-ethanol

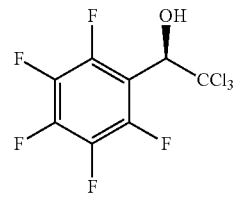

White solid in 95% yield (0.96 g, 3.04 mmol), 99.58% ee.

All physical and spectroscopic data were identical to racemic 1-perfluorophenyl-2,2,2-trichloro-ethanol. HPLC CHIRALPAK OJ-H column (5% isopropanol in hexane, 0.7 mL/min), detection: UV 210, retention time: t$_r$=7.364 min (minor), 16.486 min (major), 99.58% ee. The absolute stereochemistry was assigned by the single crystal X-ray determination.

Example 5-37: (S)-1-perfluorophenyl-2,2,2-trichloro-ethanol

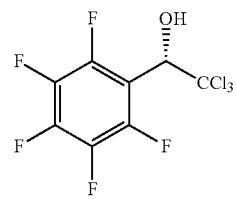

White solid in 95% yield (0.96 g, 3.04 mmol), 98.12% ee.

All physical and spectroscopic data were identical to racemic 1-perfluorophenyl-2,2,2-trichloro-ethanol. HPLC CHIRALPAK OJ-H column (5% isopropanol in hexane, 0.7 mL/min), detection: UV 210, retention time: t$_r$=7.465 min (major), 17.042 min (minor), 98.12% ee.

Example 6: Structure-Activity Relationships and Discovery of FTPs

Figure 6:
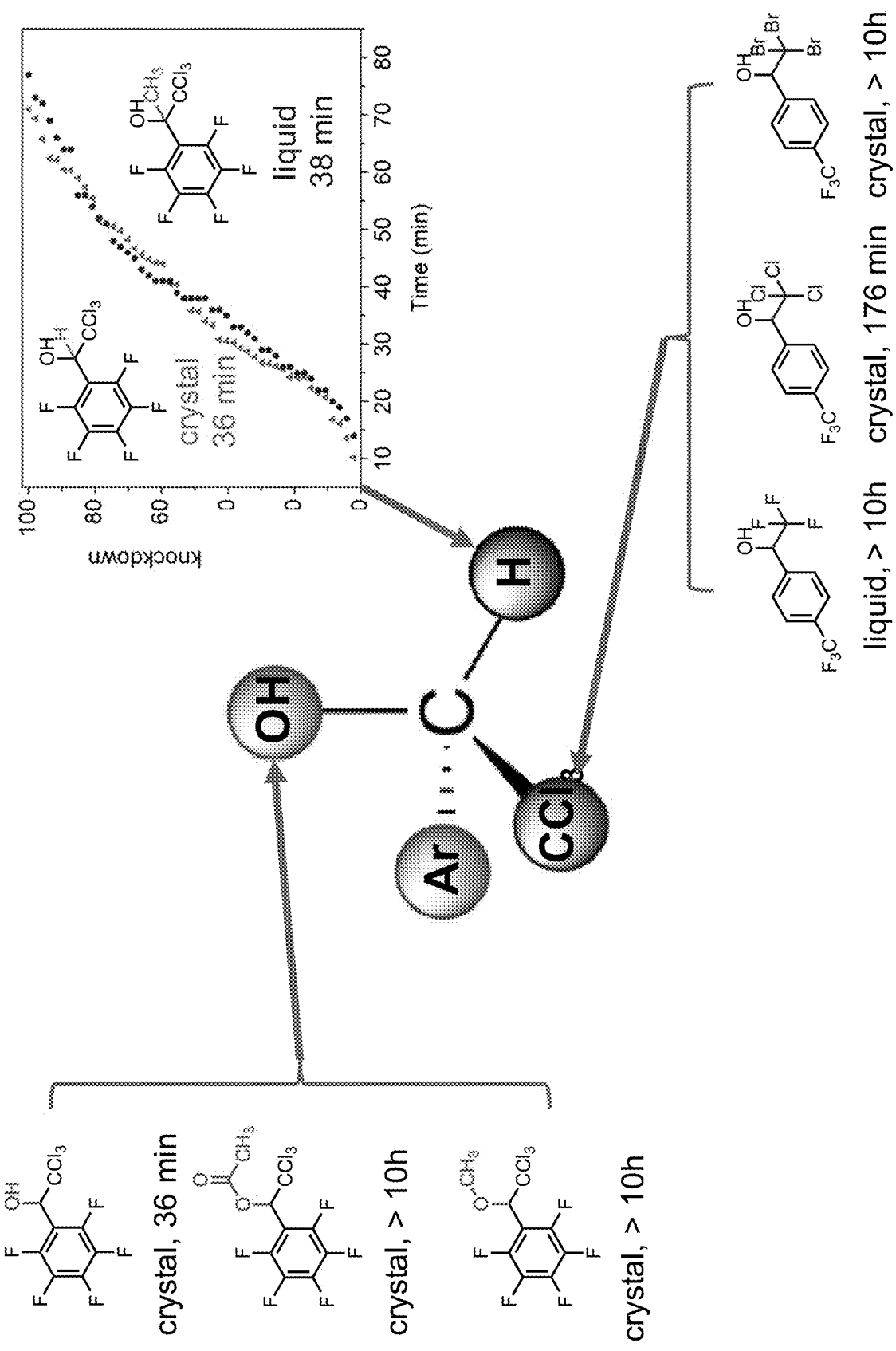
FIG. 6 illustrates the structure-activity relationships and discovery of FTPs.

The relationships between functional groups that are directly attached to the central carbon atom and *Drosophila* knockdown times are shown in FIG. 6. In FIG. 6, arrows point to the most effective functional groups. Physical state of the compound at room temperature, and the median knockdown time (KT$_{50}$) against female *Drosophila* are denoted below each compound. The dosage for the residual bioassay was $1.06*10^{-1}$ g/m$^2$.

Free alcohol was much more active against fruit flies than both ether and ester. The compound with trichloromethyl group was more lethal than that containing fluorine or bromine substituted methyl groups. Unexpectedly and surprisingly, compounds that have hydrogen or methyl bonded with the central carbon atom have very similar activities. It is notable, however, the replacement of hydrogen with methyl dramatically lower the melting temperature of the compound.

Figure 7:
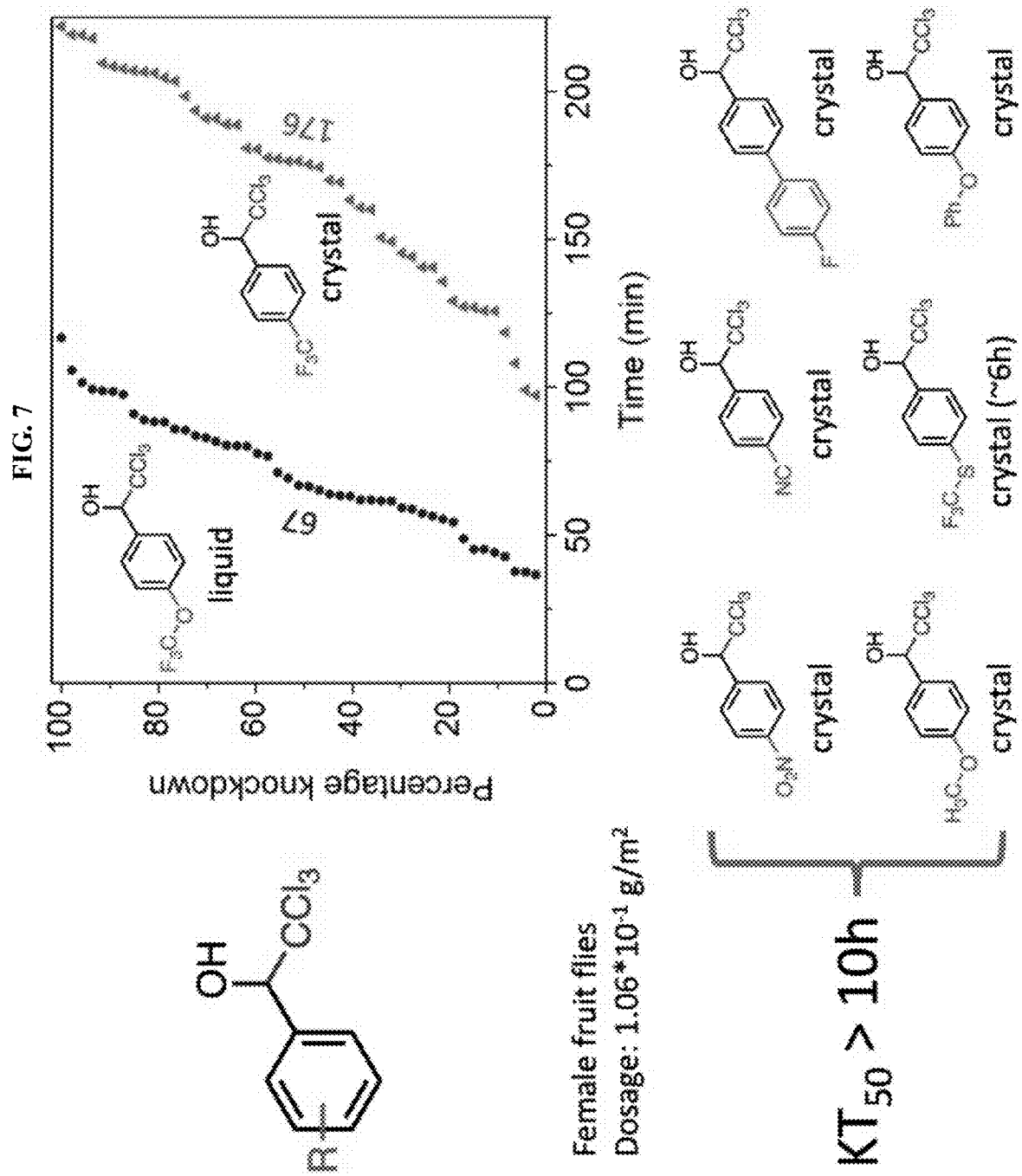
FIG. 7 illustrates the Study of relationships between functional groups on the phenyl and insecticidal activities.

The functional groups on the phenyl is more difficult to study because of a variety of possibilities. The preliminary study showed flies exposed to compounds that have common electron withdrawing functional groups and common electron donating functional groups did not show signs of intoxication after 10 hours (FIG. 7). Only the compounds with fluorine or fluorine containing functional groups, such as trifluoromethyl and trifluoromethoxy groups, had good insecticidal activities as shown in FIG. 7. In FIG. 7, physical state of the compound at room temperature, and the median knockdown time ($KT_{50}$) against female *Drosophila* are denoted below each compound. The dosage for the residual bioassay was $1.06*10^{-1}$ g/m².

Example 7: Residual Exposure Method

The example demonstrates the residual exposure method using fruit flies (*Drosophila melanogaster*) was used for the SAR study as described in Example 6. Residual action, which refers to the length of time a compound or composition may exist in a particular environment and remain effective, is a good proxy for the insecticidal activity of a compound. Each crystalline form was ground to a particle size similar to that of the liquid particles prepared by fine mist spraying. Lethality measurements were performed in duplicate for each solid-state form, each accompanied by two controls (no insecticide). Each microcrystalline form was added to a 10.0 cm diameter polystyrene petri dish (2.0 mg per dish), which was subsequently shaken to disperse the microcrystals throughout the petri dish. Amorphous forms were prepared by fine mist spraying a stock solution containing 70.0 mg of the respective insecticide in 10.0 mL hexane onto the top and bottom of 10.0 cm diameter polystyrene petri dishes (two sprays=0.280 mL) and allowing the hexane to evaporate at room temperature, resulting in 2.0 mg of liquid insecticide in each petri dish. 25 female adults *Drosophila* were sedated with carbon dioxide and flies were transferred to each petri dish. The top of the dish was then placed over the bottom and the motion of the mosquitos or fruit flies was recorded with a video camera (Sony HDR-CX455). The knockdown time was measured for each individual, with knockdown associated with an insect laying on the bottom surface of the petri dish in a supine position without moving from its original position after 10 seconds.

Figure 8:
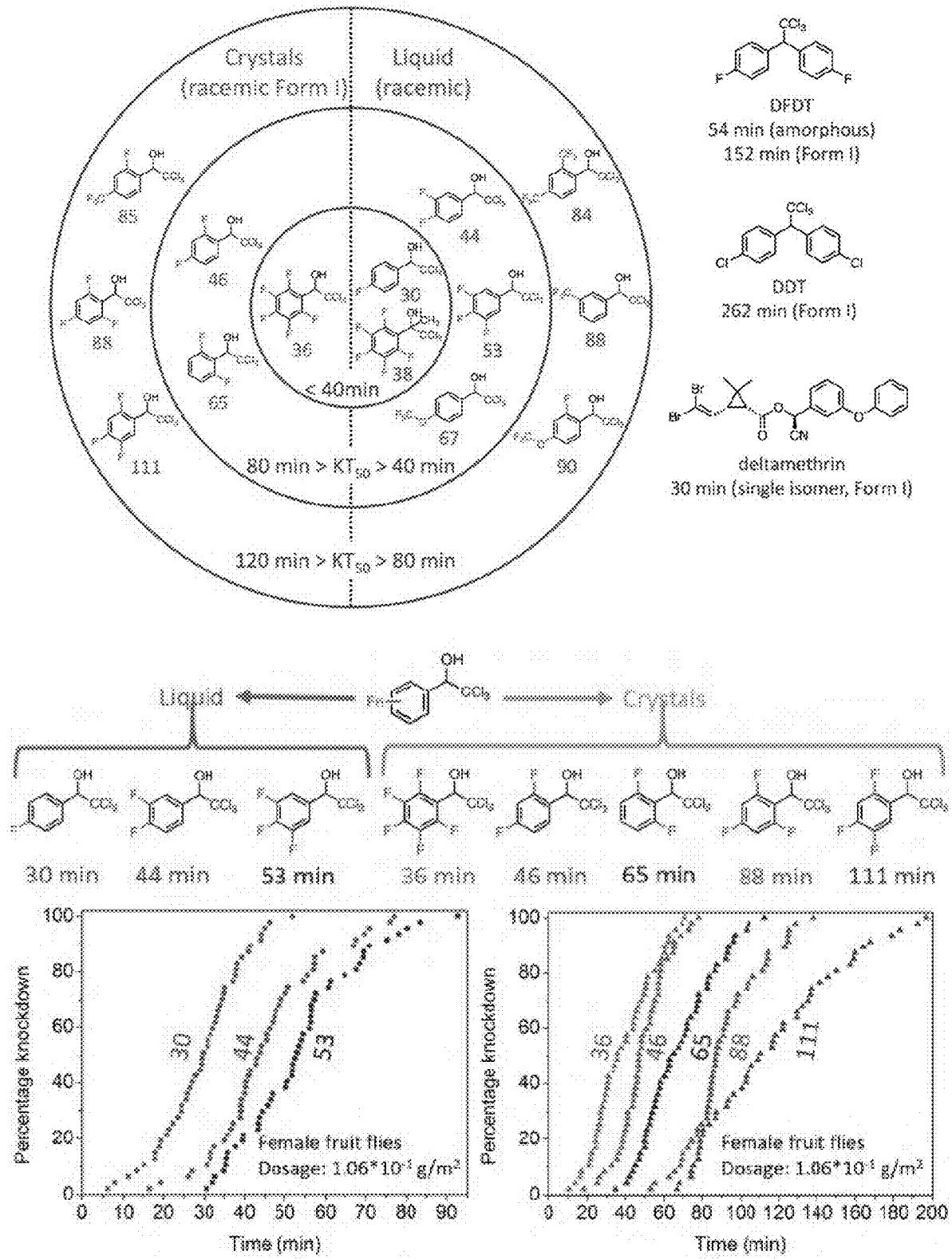
FIG. 8 illustrates the median knockdown time ($KT_{50}$) of FTEs and FTPs against female *Drosophila*.

The insecticidal activities of the compounds according to the disclosure are shown in FIG. 8. Generally, these compounds share the same scaffold, with hydrogen or methyl bonded to the central carbon atom and fluorine or fluorine containing functional groups, such as trifluoromethoxy and trifluoromethyl, on the phenyl ring. In contrast, $KT_{50}$ values for crystalline DFDT and crystalline DDT obtained using the same protocol were much larger. Deltamethrin is a single isomer of 8 possible isomers, and it's well known for very fast knockdown properties (see Casida, J. E. Michael Elliott's billion dollar crystals and other discoveries in insecticide chemistry. *Pest. Manag. Sci.* 2010, 66, 1163-1170). Insects exposed to deltamethrin quickly became paralyzed, followed by death. Notably, $KT_{50}$ values for crystalline PFTE and PFTP (perfluorophenyltrichloropropanol), and for liquid MFTE (monofluorophenyltrichloroethanol) are comparable to that of crystalline deltamethrin Form I (FIG. 8), revealing the high potency of these two classes of compounds. In FIG. 8, Physical state of the compound at room temperature, and the median knockdown time ($KT_{50}$) against female *Drosophila* are denoted below each compound. $KT_{50}$ values for Deltamethrin, DFDT and DDT obtained using the same protocol were listed for comparison. The dosage for the residual bioassay was $1.06*10^{-1}$ g/m².

Accordingly, the SAR study showed the suitability of compounds as described herein for use as insecticides.

Example 8: Acute Mammalian Toxicity

PFTE and MFTE (racemic) were tested for mammalian toxicity studies. In both cases they were classed as Category 4 compounds. That is comparatively low mammalian toxicity on par with deltamethrin. $LD_{50}$s of (RS)-MFTE and (RS)-PFTE are between 300-2000 mg/kg and, therefore, fall in GHS-Classification: Category 4 as show in Table 1.

TABLE 1

Acute toxicity hazard categories and (approximate) LD50/LC50 values defining the respective categories.

| | Category 1 | Category 2 | Category 3 | Category 4 | Category 5 |
|---|---|---|---|---|---|
| Oral (mg/kg) | 5 | 50 | 300 | 2000 | 5000 See detailed criteria |
| Dermal (mg/kg) | 50 | 200 | 1000 | 2000 | |
| Gases (ppm) | 100 | 500 | 2500 | 5000 | |

Fixed Dose Procedure (OECD Guideline 420):

(RS)-MFTE and (RS)-PFTE were test under OECD, Test No. 420: Acute Oral Toxicity—Fixed Dose Procedure, OECD Guidelines for the Testing of Chemicals, Section 4, OECD Publishing, Paris (2002), which is hereby incorporated by reference in its entirety.

Figure 12:
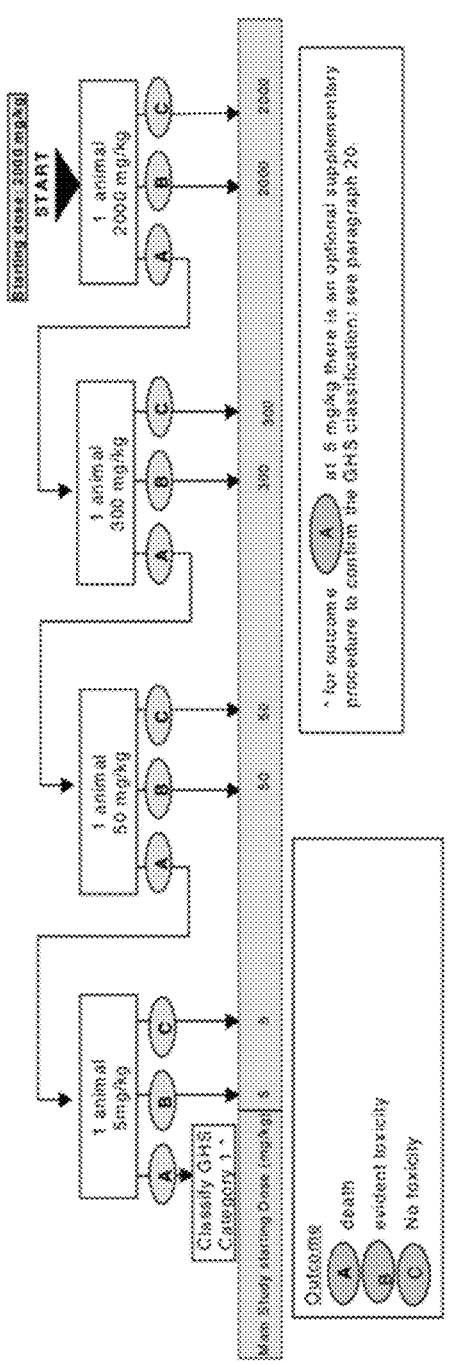
FIG. 12 illustrates the flow charts of fixed dose procedures in the sighting and main studies of LD50 of MFTE and PFTE on rats.
Figure 12:
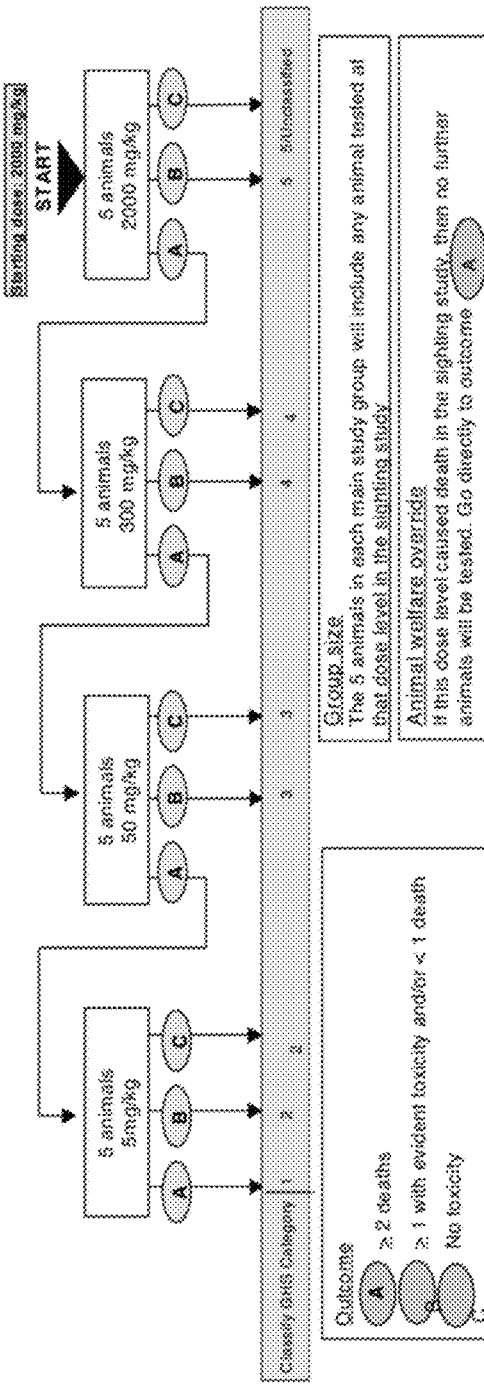

Groups of five young adult animals (rats) of one sex in a stepwise procedure using the fixed doses of 5, 50, 300 and 2000 mg/kg in the main study as shown in FIG. 12B. Single animals are used per step in the sighting study as shown in FIG. 12A. Most tests are likely to be completed with either one or two sighting study steps and one main study step, thus using between 5 and 7 animals. Up to 5 animals are used in a limit test.

$LD_{50}$ of (RS)-MFTE was determined to be between 300-2000 mg/kg (GHS-Classification: Category 4). (RS)-MFTE used of the test was in liquidus form and its purity was 98% by weight. The animal dosed at 2000 mg/kg b.w. in the pilot experiment had to be euthanized 1 day after application due to severity of symptoms (lethargy/unconsciousness, prostration). Upon necropsy, changes were seen mainly in the gastrointestinal tract: dilation of the stomach, small intestine and caecum, slimy contents. The colon was completely empty. The adrenal glands appeared slightly enlarged. The 5 animals dosed at 300 mg/kg b.w showed only mild symptoms (underactivity). Upon necropsy, no relevant changes were noted except for the spleen (spleen sections showed small white spots in 4 animals, indicative of a mild hyperplasia).

$LD_{50}$ of (RS)-PFTE is between 300-2000 mg/kg b.w. (GHS-Classification: Category 4), as was for the MFTE. (RS)-PFTE used of the test was racemic Form I, ($P2_1$, m.p.=62° C.) and its purity was purity=99% by weight. The animal dosed at 2000 mg/kg b.w. in the pilot experiment had to be euthanized on day 1 approx. 3 h after application due to severity of symptoms (Lethargy, decreased respiration, sunken flanks, hunched posture, piloerection, partially closed eyes, lachrymation). Upon necropsy, changes were seen mainly in the gastrointestinal tract: distension of the stomach and small intestine, liquid content in the small intestine/hard content in the caecum. The animals treated with 300 mg/kg b.w. had no clinical symptoms except for soft feces approximately 2 h after application, and there were no abnormal findings during necropsy. The results showed that rat $LD_{50}$ of (RS)-PFTE and (RS)-MFTE are both between 300-2000 mg/kg (GHS-Classification: Category 4). Therefore, (RS)-PFTE and (RS)-MFTE has relatively low mammalian toxicity compared with most currently commercial insecticides, such as deltamethrin, pyrethrins, organophosphates and methylcarbamates, suggesting (RS)-PFTE and (RS)-MFTE might be more selective on insects than mammals. Unexpectedly and surprisingly, PFTE, MFTE and other studied compounds as described herein are not only potent insecticides, but also safe chemical compounds for human and other mammals in terms of acute toxicity. This is coincident with green chemistry and modern concepts in the development of new insecticides.

Example 9: Study of Enantioselective Lethality of FTEs and FTPs

The example demonstrates that enantiomers of FTEs as described herein have different potencies in insecticidal activities.

Single enantiomers of MFTE and PFTE (Examples 5-34 to 5-37) were prepared with the procedures as described in Scheme 5. Single crystal X-ray analysis is used for the assignment of absolute configuration of enantiomers. These enantiomers of MFTE and PFTE and the racemic thereof were test for lethality against fruit flies (*Drosophila melanogaster*) and the $KT_{50}$ for each enantiomer and racemic were measured.

Figure 9:
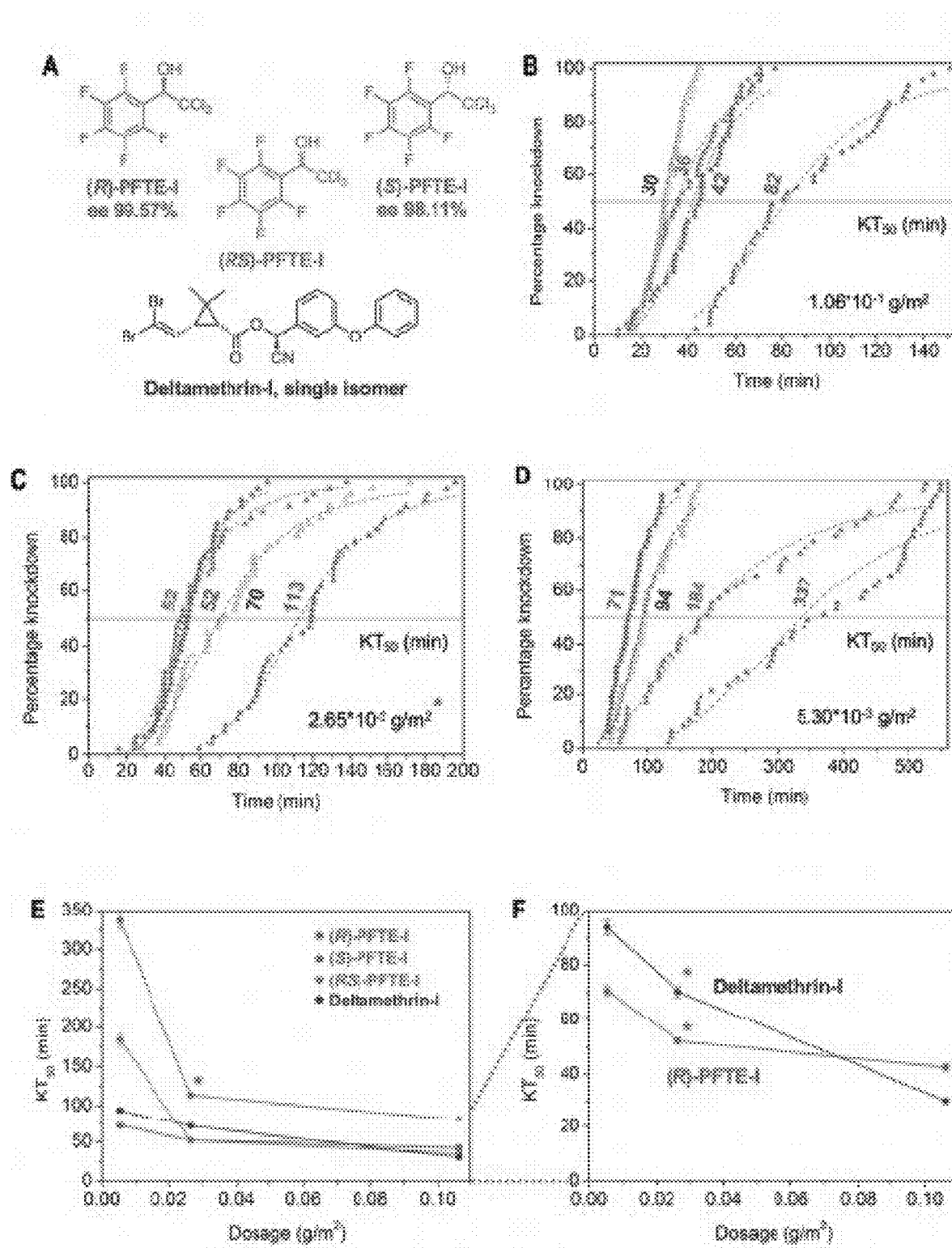
FIG. 9 illustrates the enantioselectivity lethality of PFTE against female *Drosophila*.
Figure 11:
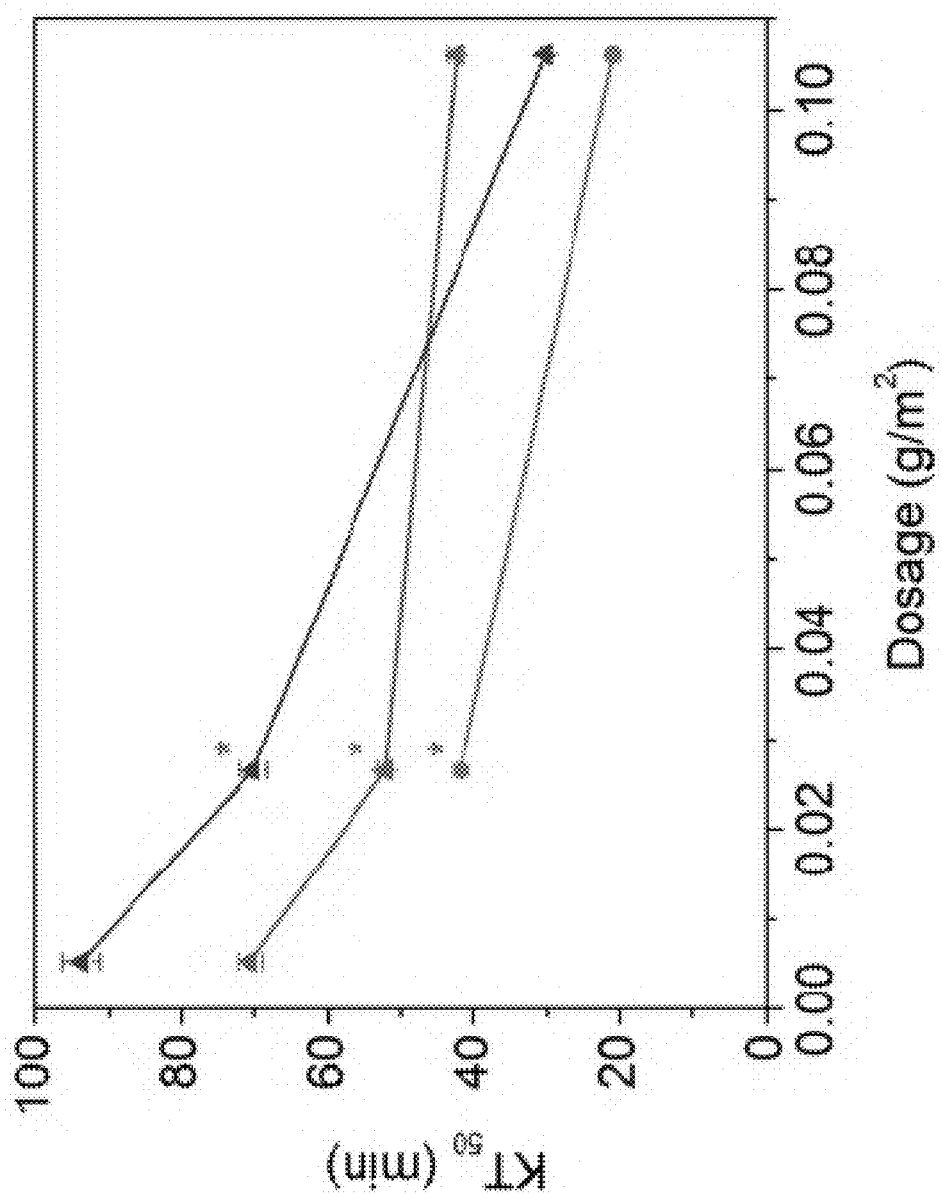
FIG. 11 illustrates the lethality of (R)-enantiomers of MFTE and PFTE against female *Drosophila*.

Racemic ((RS)-PFTE and enantiomerically pure PFTE (R)/(S)-PFTE are all in crystalline form. X-ray determination showed they have the same crystal structures, with the space group $P2_1$. Their respective lethalities and the comparison with deltamethrin at different dosages are shown in FIG. 9. (R)-PFTE is always faster in action than (S)-PFTE as shown in FIGS. 9b and 9c. This is consistent with the results of MFTE, suggesting the enantiomeric lethality of this kind of compounds, R enantiomers might be more lethal than S enantiomers. (R)-PFTE is faster in action than (RS)-PFTE at the dosage below $1.06*10^{-1}/m^2$ as shown in FIG. 9b. Unexpectedly and sparingly, (R)-PFTE is faster in action than deltamethrin at low dosage $5.30*10^{-3}/m^2$, despite (R)-PFTE is slower in action than deltamethrin Form I against fruit flies at high dosage $1.06*10^{-1}/m^2$ and above as shown in FIG. 9c and FIG. 11.

Figure 10:
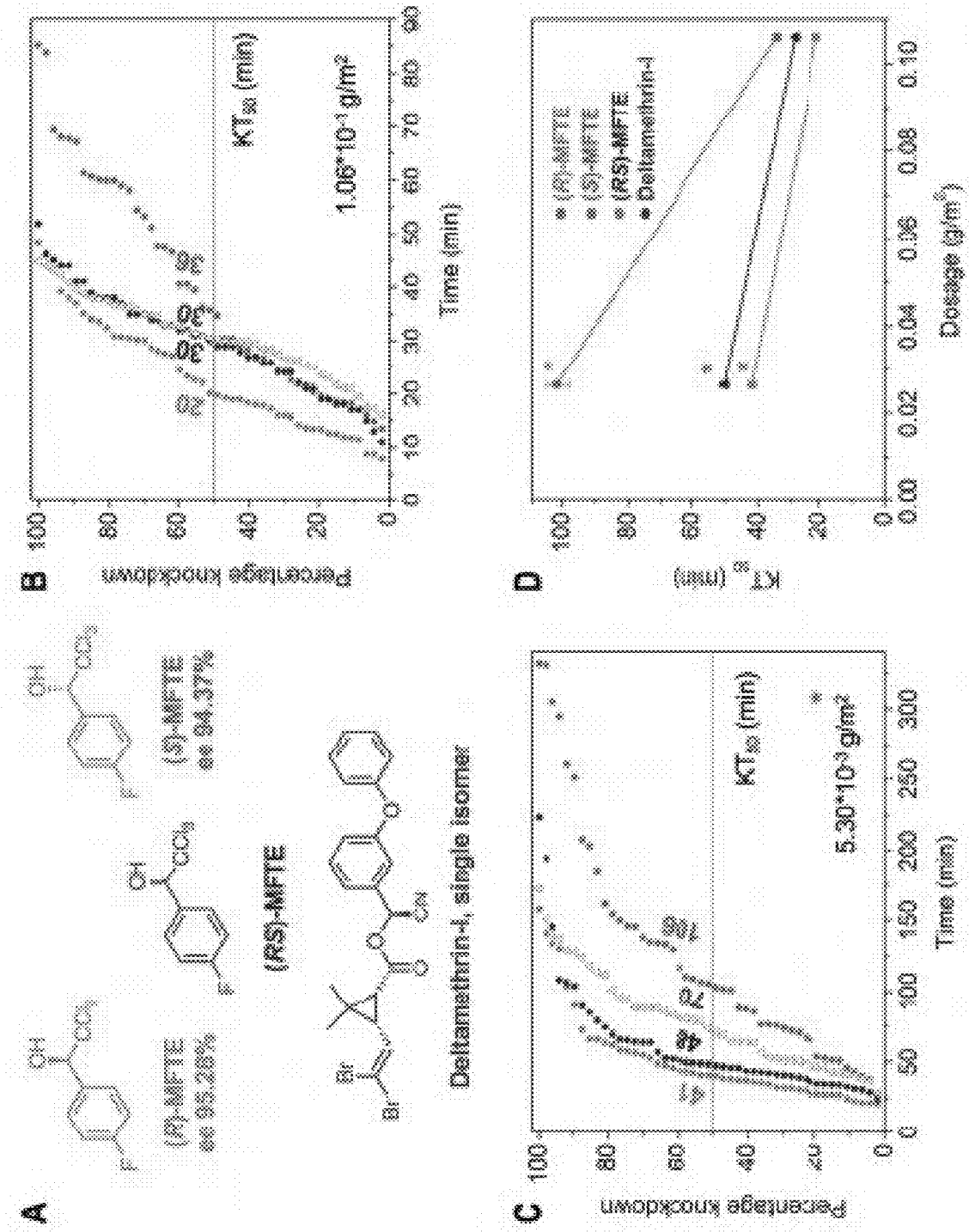
FIG. 10 illustrates the enantioselectivity lethality of MFTE against female *Drosophila*.

Racemic ((RS)-MFTE and enantiomerically pure MFTE (R)/(S)-MFTE are all liquid. Their respective lethalities and the comparison with deltamethrin at different dosages are shown in FIG. 10. (R)-MFTE is always faster in action than (S)-MFTE, and (RS)-MFTE lies in between of (R) and (S)-MFTE in lethality as shown in FIGS. 10B and 10C. Unexpectedly and surprisingly, (R)-MFTE is even faster in action than deltamethrin Form I against fruit flies, at the dosage above $5.30*10^{-3}/m^2$ as shown in FIG. 10C and FIG. 11.

Enantiomers FTPs, however, are tertiary alcohols, which are expected to be resolved by chromatography with chiral columns. Enantiomers of FTPs are expected to show different potencies in insecticidal activities.

Example 10: Mode of Action Studies

About 85% of insecticides nowadays in global market act on the nerve of insects. Compounds including FTEs and FTPs are tested for the specific target site on insect neurons. The observation on the fruit flies that FTEs and FTPs induced hyperactivity followed by paralysis, and then death demonstrates that they are neurotoxins as well.

Example 11: Median Lethal Dose (LD50) on Different Insects

Compounds including FTEs and FTPs as described herein demonstrate selectivities against different insects.

Another important criterion for the evaluation of insecticides is selectivity. The selectivity of an insecticide is generally expressed by the ratio, which are based on the topical $LD_{50}$ (µg/g (=mg/kg)) for insects/acute oral $LD_{50}$ (mg/kg) for the rat. The acute oral $LD_{50}$ of the compounds as described herein for the rats; the $LD_{50}$ for insects will be obtained from topical application according to the WHO guideline (see World Health Organization, Guidelines for Efficacy Testing of Insecticides for Indoor and Outdoor Ground-Applied Space Spray Applications 2009). Take mosquitos for example.

A constant volume of 0.1 µl or less insecticide solutions (highly volatile solvents such as acetone will be used) of the compounds described herein will be delivered to the pronotum of female mosquitos using an automatic pipetting device. After dosing, mosquitos is transferred into clean holding cups and provided with 10% sugar solution on cotton wool and held for 24 hours at 27±2° C. temperature and 80±10% RH. Mortality of treated mosquitos is recorded after 24 hours. Finally, statistical analysis is used to calculate the $LD_{50}$ for mosquitos. Disease vectors, such as mosquitos and other agricultural pest insects are tested.

Example 12: Identify Metastable Forms of FTEs and FTPs and Evaluate their Lethality Against Insects The metastable forms of the compounds as described herein including FTEs and FTPs are expected to be identified and the potential metastable forms of FTEs and FTPs are expected to be more active than their respective known crystalline forms.

To fully study their polymorphism, solvent-based screening methods are applied for the compounds as described herein, whose unique forms will be efficiently distinguished by Raman spectroscopy or powder X-ray diffraction. Melt crystallization methods to achieve high driving force, low crystal nucleation rate, and slow growth are used for the discovery of remaining potential metastable forms. In addition, polymers or small molecules are used as substrates to explore substrate-induced heterogeneous nucleation of new forms according to Lopez-Mejiás et al. (Lopez-Mejías, V.; Kampf, J. W.; Matzger, A. J. Polymer-induced nucleation of tolfenamic acid: structural investigation of a pentamorph. *J. Am. Chem. Soc.* 2009, 131, 4554-4555), which is hereby incorporated by reference in its entirety. Single crystals of newly discovered forms are prepared from the evaporation of solutions or from the melt, and their crystal structures are solved by means of single-crystal X-ray diffraction. In order to compare the relative thermodynamic stabilities of newly identified and previous known forms, monitored is the structural transformation between single crystals as well as between powders at various temperature using microscope and X-ray diffraction. After the detailed characterization of new polymorphs, each form is prepared with similar particle sizes and the lethality thereof against disease vectors or agricultural pest insects is measured by means of residual exposure bioassay.

Example 13: Study of Photo Stability and Chemical Stability of FTEs and FTPs

Compounds including FTEs and FTPs as described herein are expected to have photo stability and chemical stability. For example, FTEs and FTPs are tested for photo stability and chemical stability as described herein. FTEs and FTPs are exposed to lights in that range of wavelengths using a simulated sunlamp for the photo stability testing. The chemical composition of compounds is analyzed regularly using NMR and/or other characterization techniques to determine their half-life time under these conditions. In order to test the chemical stability of these compounds, pH values of the testing environment is adjusted according to the correspondent decomposition conditions. In addition, an oxygen-saturated aqueous solution is used for the stability testing to mimic the raining condition. Other testing methods are applied as appropriate to mimic field application.

What is claimed is:

1. A compound according to Formula (I):

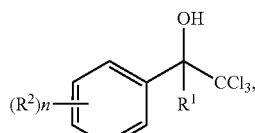

or a pesticidally acceptable salt thereof, wherein:
$R^1$ is selected from —H and —$CH_3$;
$R^2$ is independently at each occurrence selected from —F, —$OCF_3$, and —$CF_3$;
wherein when $R^1$ is —H, $R^2$ is not —F at each occurrence;
n is an integer from 1 to 5,
with the proviso that the compound according to Formula (I) is not:

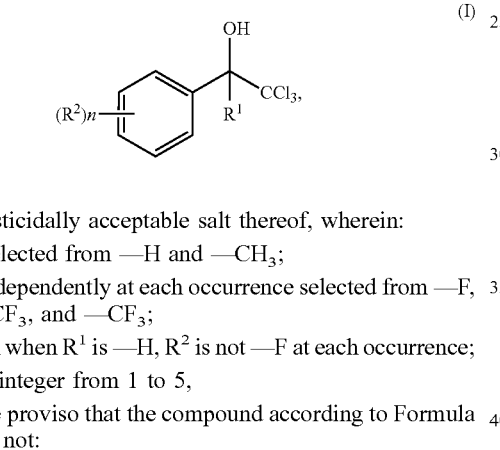

2. The compound according to claim 1, wherein $R^1$ is H and $R^2$ is independently at each occurrence selected from —$OCF_3$, and —$CF_3$.

3. The compound according to claim 1, wherein $R^1$ is —$CH_3$.

4. The compound according to claim 3, wherein $R^2$ is —F.

5. The compound according to claim 1, wherein $R^2$ is —$OCF_3$.

6. The compound according to claim 1, wherein $R^2$ is —$CF_3$.

7. The compound according to claim 1 selected from the group consisting of:

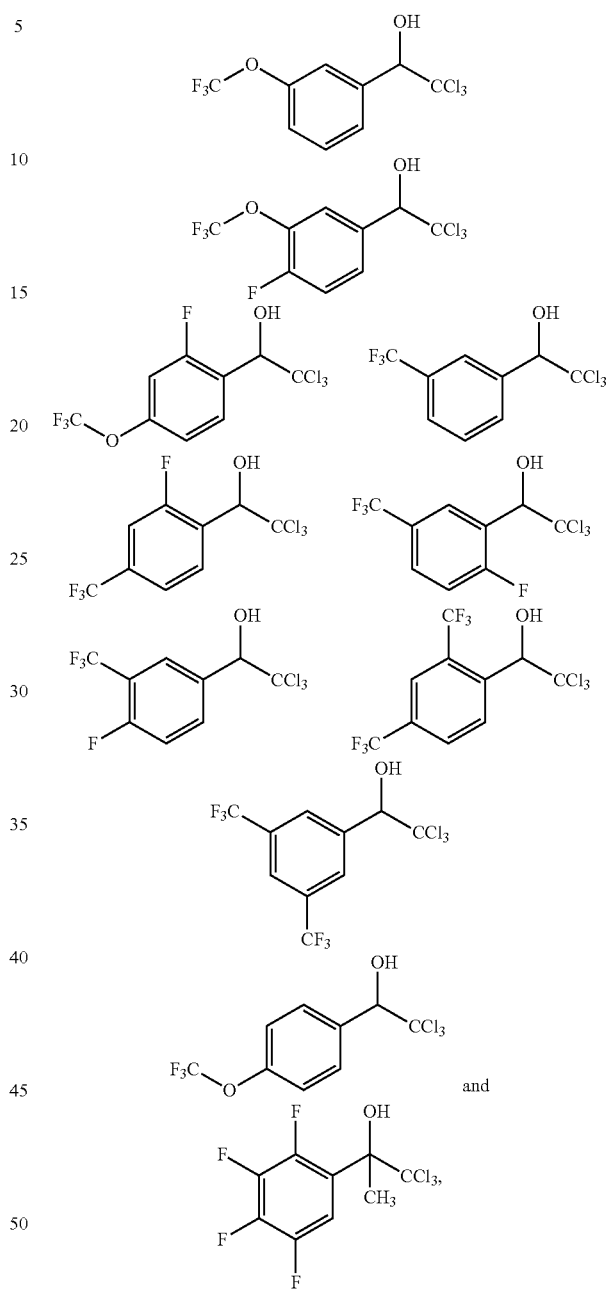

or a pesticidally acceptable salt thereof.

8. A pesticidal composition comprising the compound according to claim 1, wherein the composition comprises a racemic mixture of the compound.

9. The pesticidal composition comprising the compound according to claim 1, wherein the composition comprises an enantioenriched mixture of the compound.

10. The pesticidal composition comprising the compound according to claim 1, wherein the compound is present in an enantiomeric excess of about 90% or more.

11. A method of controlling a pest comprising applying to the pest or its locus the compound according to claim 1.

12. The method according to claim 11, wherein $R^1$ is —H and $R^2$ is independently at each occurrence selected from —OCF$_3$, and —CF$_3$.

13. The method according to claim 11, wherein $R^1$ is —CH$_3$.

14. The method according to claim 12, wherein $R^2$ is —F.

15. The method according to claim 11, wherein $R^2$ is —OCF$_3$.

16. The method according to claim 11, wherein $R^2$ is —CF$_3$.

17. The method of claim 11, wherein the pest is an insect.

18. The method of claim 17, wherein the insect is selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas (indoors & outdoors), flea beetles, flies, flesh flies, fruit flies, fungus gnats (sciarid flies), gnats, grasshoppers, green bottle flies, greenstriped mapleworms, ground beetles, gypsy moths (larvae), hide beetles, house flies, hornets, horseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, redhumped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellownecked caterpillar, wasps, and webworms.

* * * * *

UNITED STATES PATENT AND TRADEMARK OFFICE
CERTIFICATE OF CORRECTION

PATENT NO. : 11,570,987 B2
APPLICATION NO. : 17/033317
DATED : February 7, 2023
INVENTOR(S) : Xiaolong Zhu et al.

It is certified that error appears in the above-identified patent and that said Letters Patent is hereby corrected as shown below:

In the Claims

At Column 55, Line 6, please replace Claim 14 with the following:
14. The method according to claim 13, wherein $R^2$ is -F.

Signed and Sealed this
Tenth Day of September, 2024

Katherine Kelly Vidal
*Director of the United States Patent and Trademark Office*